(12) United States Patent
Porro et al.

(10) Patent No.: US 11,937,924 B2
(45) Date of Patent: Mar. 26, 2024

(54) DEVICE AND METHOD FOR MEASURING BLOOD PARAMETER

(71) Applicant: DATAMED S.R.L., Peschiera Borromeo (IT)

(72) Inventors: Giampiero Porro, Dizzasco (IT); Alessandro Torinesi, Ornago (IT); Roberto Pozzi, Milan (IT); Giovanna Quarto, Vimodrone (IT); Luca Bolzoni, Milan (IT)

(73) Assignee: DATAMED S.R.L., Peschiera Borromeo (IT)

(*) Notice: Subject to any disclaimer, the term of this patent is extended or adjusted under 35 U.S.C. 154(b) by 0 days.

(21) Appl. No.: 18/274,545

(22) PCT Filed: Feb. 25, 2022

(86) PCT No.: PCT/IB2022/051680
§ 371 (c)(1),
(2) Date: Jul. 27, 2023

(87) PCT Pub. No.: WO2022/200875
PCT Pub. Date: Sep. 29, 2022

(65) Prior Publication Data
US 2024/0032829 A1 Feb. 1, 2024

(30) Foreign Application Priority Data
Mar. 26, 2021 (IT) .................. 102021000007418

(51) Int. Cl.
A61B 5/1455 (2006.01)
A61M 1/36 (2006.01)
(Continued)

(52) U.S. Cl.
CPC ....... A61B 5/14557 (2013.01); A61M 1/3609 (2014.02); G01N 21/6408 (2013.01);
(Continued)

(58) Field of Classification Search
CPC ............ A61B 5/14557; A61M 1/3609; A61M 2230/205; G01N 21/6408; G01N 21/85; G01N 2021/6482; G01N 2201/1296
(Continued)

(56) References Cited

U.S. PATENT DOCUMENTS 9,541,539 B2 1/2017 Machuca et al.
2010/0171043 A1 7/2010 Burke et al.
2020/0309699 A1 10/2020 Frischauf et al.

OTHER PUBLICATIONS

International Search Report & Written Opinion in PCT/IB2022/051680 dated Jun. 13, 2022.

Primary Examiner — Md M Rahman
(74) Attorney, Agent, or Firm — Manelli Selter PLLC; Edward Stemberger

(57) ABSTRACT

The present invention refers to a device (1) and a method of measuring a parameter of blood, preferably correlated to the presence or concentration of oxygen in blood. The invention provides to: excite a photosensitive element (18') in contact with blood by excitation pulses, detect light responses of the photosensitive element corresponding to the excitation pulses, and analyze the plurality of luminescence decay curves at least two time windows (t1-tN). Moreover, the invention provides to: detect one or more light answer analog information regarding the luminescence curve decay at each time window, convert the analog information into digital data, process the digital data and the actual temperature value of blood by taking into account a plurality of data of previous measures of the parameter of blood performed during a previous training, and determine, as a result of the processing step, at least one value of said parameter of blood.

20 Claims, 10 Drawing Sheets

(51) Int. Cl.
  *G01N 21/64* (2006.01)
  *G01N 21/85* (2006.01)
(52) U.S. Cl.
  CPC ....... *G01N 21/85* (2013.01); *A61M 2230/205* (2013.01); *G01N 2021/6482* (2013.01); *G01N 2201/1296* (2013.01)
(58) Field of Classification Search
  USPC .......................................................... 356/41
  See application file for complete search history.

DEVICE AND METHOD FOR MEASURING BLOOD PARAMETER

TECHNICAL FIELD OF THE INVENTION

The present invention refers to a device and a method for measuring a parameter of blood, particularly a parameter correlated to the presence or concentration of oxygen in blood.

The device and method according to the invention enable to measure the parameter in a blood extracorporeal circuit.

Moreover, the present invention refers to a use of the device and to an apparatus comprising the device.

PRIOR ART

Probes for measuring the concentration of oxygen in blood, apt to be used in a blood extracorporeal circuit are known.

A probe of this type is known from the U.S. Pat. No. 6,009,339, which refers to a probe provided with sensors apt to come in contact with blood, which require to be calibrated before being used in a clinical setting of the probe.

Further, it is noted, particularly with reference to a measure of the oxygen partial pressure in blood, that the present commercially available systems which measure such parameter require one or more calibration points in order to provide an accurate measure.

Generally, the calibration requires some calibration time before being able to use the probe or system; the requirement of calibrating the probe is therefore disadvantageous because it does not enable a prompt use of the probe. For example, a probe to be calibrated cannot be used quickly and effectively in emergency conditions, wherein the timeliness of a measure could be crucial for a patient.

OBJECTS OF THE INVENTION

Therefore, a main object of the present invention consists of providing a device for measuring a parameter of blood capable of overcoming the inconveniences previously described with reference to the prior art.

The object of the present invention is to provide a device for measuring a blood parameter which does not require calibration by the end user prior to use.

It is a further object of the invention to provide a method enabling to measure a parameter of blood without performing a calibration step before a measure.

An additional object of the invention consists of proposing a device and method enabling to measure rapidly, effectively and reliably a parameter of blood.

It is a further object of the invention to provide a device capable of performing a highly precise and autonomous measurement of a blood parameter in the whole measure field of the parameter.

These and other objects are met by a device, a use of the device, an apparatus and by one or more methods according to the following descriptions, the attached claims and to the following aspects.

SUMMARY OF THE INVENTION

Some aspects of the invention will be herein described. When an aspect and/or a claim refers, by a specific dependence, to one or more other aspects or claims and/or by words such as "the" or "said" and similar to one or more elements or steps or operations introduced by another aspect or claim, such aspect/s and/or such claim/s can be considered in combination with each other.

The invention provides a probe for measuring a parameter of blood supplied with a control unit enabling it to measure the parameter based on a plurality of data of previous measures of said parameter performed during a previous training.

The control unit implements the intelligence of the device and is dedicated to autonomously perform the measure. For obtaining that, the control unit comprises a computing model (coded by a program code) obtained by a plurality of data of previous measures of the parameter of blood performed during a previous training. Substantially, the probe learns from a previous training and consequently, when it is in clinical use conditions, is readily available to be used without requiring a previous calibration.

In order to train the probe to measure a specific parameter it is advantageous that the chemical composition of the photosensitive element employed in the clinical use (this chemical composition determining the light response to excitations) is the same or substantially the same as the chemical composition of the photosensitive elements used during the training. By using the same chemical composition of the photosensitive elements both during the training and during the clinical use, the probe learns, during the training, to recognize the values of the parameter in determined conditions; when the same or similar conditions repeatedly occur in the clinical use, the probe is capable of recognizing them and determining the value of the parameter (by the program code), consequently measuring the parameter.

Numbered aspects of the invention follow.

1. Device for measuring a parameter of blood, preferably correlated to the presence or concentration of oxygen in blood, comprising:
   a probe configured to excite a photosensitive element by a series of excitation pulses,
   a container apt to contain blood and/or in which blood can flow,
   an optical interface provided with a photosensitive element apt to respond, at the end of an excitation which is subjected to when is in contact with blood, with a light response, the light response providing a luminescence decay curve, in operative conditions the photosensitive element being in contact with blood,
   the probe and the container being structured to be coupled, the probe comprising a photodetector configured to detect, in operative conditions of the device, a plurality of light responses of the photosensitive element corresponding to a series of excitation pulses.

2. Device for measuring a parameter of blood, preferably correlated to the presence or concentration of oxygen in blood, comprising:
   a box body,
   a coupling portion associated to the box body and configured to be coupled to a container apt to contain blood and/or in which the blood can flow, the container being associated to a photosensitive element apt to respond, at the end of an excitation which is subjected to when it is in contact with blood, with a light response, the light response providing a luminescence decay curve, in operative conditions the photosensitive element being in contact with blood,
   an excitation member housed inside the box body and configured to excite said photosensitive element by a series of excitation pulses,
   a photodetector housed inside the box body and configured to detect in operative conditions of the device, a plurality of light responses of the photosensitive element corresponding to the series of excitation pulses, the light responses providing luminescence decay curves.

3. Device for measuring a parameter of blood, preferably correlated to the presence or concentration of oxygen in blood, comprising:
   a box body,
   a coupling portion associated to the box body and configured to have:
      a coupled configuration in which it is coupled to a container,
      a decoupled configuration in which it is not coupled to a container,
   a container, for example a tubular element, apt to contain blood and/or in which blood can flow, the container being configured to be coupled to said coupling portion,
   a photosensitive element associated to the container and apt to respond, at the end of an excitation, which is subjected to when is in contact with blood, with a light response, the light response providing a luminescence decay curve, in operative conditions the photosensitive element being in contact with blood,
   an excitation member housed inside of the box body and configured to excite said photosensitive element by a series of excitation pulses,
   a photodetector housed inside of the box body and configured to sense, in operative conditions of the device, a plurality of light responses of the photosensitive element corresponding to the series of excitation pulses, the light responses providing luminescence decay curves.

4. Device for measuring a parameter of blood, preferably correlated to the presence or concentration of oxygen in blood, comprising:
   a box body,
   a photosensitive element apt to respond, at the end of an excitation which is subjected to when it is in contact with blood, with a light response, the light response providing a luminescence decay curve, in operative conditions the photosensitive element being in contact with blood,
   an excitation member housed inside of the box body and configured to excite said photosensitive element by a series of excitation pulses,
   a photodetector housed inside of the box body and configured to detect, in operative conditions of the device, a plurality of light responses of the photosensitive element corresponding to the series of excitation pulses, the light responses providing luminescence decay curves.

5. Aspect according to one of the preceding aspects, the device further comprising a control unit configured to perform the following operations:
   processing light response digital data and the actual temperature value of blood, optionally by taking into account a plurality of data of previous measures of said parameter of blood performed during previous training,
   determining, as a result, at least one value of said blood parameter.

6. Aspect according to one of the preceding aspects, the device further comprising a control unit housed inside of the box body and configured to perform the following operations:
   receiving, for each of at least two time windows of analysis of each luminescence curve, one or more light response analog information regarding the luminescence decay curve,
   converting the light response analog information, detected at least two time windows for each light response, into light response digital data,
   processing said light response digital data and the actual temperature value of blood by taking into account a plurality of data of previous measures of said blood parameter performed during a previous training,
   determining, as a result of the processing operation, at least one value of said blood parameter.

7. Aspect according to one of the preceding aspects, the device further comprising a control unit, preferably housed inside of the box body, configured to determine the value of said blood parameter based on an analysis in the time domain of light response information of the photosensitive element.

8. Device for measuring a parameter of blood, preferably correlated to the presence or concentration of oxygen in blood, comprising:
   a box body,
   a coupling portion associated to the box body and comprising at least one coupling element, the coupling portion being configured to feature:
      a coupled configuration in which it is coupled to a container by said at least one coupling element,
      a decoupled configuration in which it is not coupled to a container,
   a container, for example a tubular element, apt to contain blood and/or inside of which blood can flow, the container being configured to be coupled to said coupling portion,
   a photosensitive element associated to the container and apt to respond, at the end of an excitation, which is subjected to when it is in contact with blood, with a light response, the light response providing a luminescence decay curve, in operative conditions the photosensitive element being in contact with blood,
   an excitation member housed inside of the box body and configured to excite said photosensitive element by a series of excitation pulses,
   a photodetector housed inside of the box body and configured to detect, in operative conditions of the device, a plurality of light responses of the photosensitive element corresponding to the series of excitation pulses, the light responses providing luminescence decay curves,
   a control unit housed inside of the box body and configured to perform the following operations:
      receiving, for each of at least two time windows of analysis of each luminescence curve, one or more light response analog information regarding the luminescence decay curve,
      converting the light response analog information, detected at least two time windows for each light response, into light response digital data,
      processing said light response digital data and the actual temperature value of blood by taking into account a plurality of data of previous measures of said blood parameter performed during a previous training,
      determining, as a result of the processing operation, at least one value of said blood parameter.

9. Aspect according to one of the preceding aspects, in operative conditions of the device the photosensitive element responding at the end of each excitation pulse with said light response.

10. Aspect according to one of the preceding aspects, wherein the previous training is performed on a plurality of photosensitive elements of the same type as the photosensitive element of the device.

11. Aspect according to one of the preceding aspects, the photosensitive element having a determined chemical composition, preferably the photosensitive element being a photosensitive substance.

12. Aspect according to the aspect 11, the control unit being configured to consider a plurality of data of previous measures of said blood parameter performed during previous training carried out by using a plurality of photosensitive elements having the same chemical composition.

13. Aspect according to one of the preceding aspects, the device being apt to measure the partial pressure of oxygen in blood.

14. Aspect according to one of the preceding aspects, said parameter being the partial pressure of oxygen in blood.

15. Aspect according to one of the preceding aspects, the device comprising a temperature sensor housed inside of the box body and configured to measure the actual temperature value of blood.

16. Aspect according to the aspect 15, the effective or actual temperature of blood being the temperature of blood in said container.

17. Aspect according to one of the preceding aspects, the control unit being configured to:
determine, as a result of the processing operation, a value of said parameter at the actual temperature of blood, and
determine, as a result of the processing operation, a value of said parameter at a reference temperature of blood, for example at 37° C.

18. Aspect according to one of the preceding aspects, the control unit being configured to measure the parameter correlated to the presence or concentration of oxygen in blood without requiring an initial calibration of the device.

19. Aspect according to one of the preceding aspects, the device being of a ready-to-use and/or plug-and-play type.

20. Aspect according to one of the preceding aspects, said device being useable without requiring an initial calibration.

21. Aspect according to one of the preceding aspects, said device being calibrated during previous laboratory training.

22. Aspect according to one of the preceding aspects, the control unit being configured to perform said operations in a time in the order of microseconds.

23. Aspect according to one of the preceding aspects, the previous measures of said parameter of blood deriving from a previous training.

24. Aspect according to one of the preceding aspects, the control unit being configured to consider a plurality of data of previous measures of said blood parameter performed during a previous training by a program code based on machine learning and obtained by previous training.

25. Aspect according to one of the preceding aspects, wherein the machine training, and therefore the program code, is calibrated on the chemical composition of the photosensitive element.

26. Aspect according to one of the preceding aspects, the program code being or corresponding to a code or machine language.

27. Aspect according to one of the preceding aspects, the control unit being configured to process said light response digital data and said actual temperature value of blood by taking into account a plurality of data of previous measures of said blood parameter by an algorithm, preferably the algorithm being derived from previous training.

28. Aspect according to the aspect 27, the algorithm deriving from previous training being based on learning, preferably machine learning, the training and the learning being before the use of the device, preferably during a plurality of training periods.

29. Aspect according to the aspect 27 or 28, the control unit featuring a code or machine language and said algorithm based on learning being implemented in said code or machine language.

30. Aspect according to one of the aspects from 24 to 29, wherein the control unit comprises at least one microprocessor, said program code and/or said algorithm being implemented by code or machine language in the microprocessor, preferably by a code C.

31. Aspect according to one of the aspects from 27 to 30, the algorithm mapping sets of input data to a set of suitable output data.

32. Aspects according to one of the aspects from 27 to 31, the algorithm featuring at least two suitable output data, said two suitable output data providing:
the value of said parameter at the effective temperature of blood, and
the value of said parameter at a reference temperature of blood, for example at 37° C.

33. Aspect according to one of the aspects from 27 to 32, the control unit being configured, by said algorithm, to perform one or more of the following operations:
analyzing said light response digital data and said actual temperature value of blood by a matrix mathematical model, and/or
fitting said light response digital data and said blood actual temperature value to the plurality of data of previous measures.

34. Aspect according to one of the preceding aspects, the coupling portion and the container comprising corresponding coupling elements configured to be coupled in the coupled configuration.

35. Aspect according to one of the preceding aspects, the coupling portion and the container comprising at least one respective coupling element of a first type.

36. Aspect according to the aspect 35, the first type coupling element enabling an initial placement, for example by coupling the container to the device.

37. Aspect according to the aspect 35 or 36, the first type coupling elements being configured to enable a mechanical type engagement of the container with the coupling portion of the device.

38. Aspect according to the aspect 35 or 36 or 37, the first type coupling element of the container comprising a slit and the first type coupling element of the coupling portion comprises a tab or hook structured to engage at said slit.

39. Aspect according to one of the preceding aspects, the coupling portion and the container comprising at least one respective coupling element of a second type.

40. Aspect according to the aspect 39, the second type coupling elements enabling a correct univocal placement, for example by snapping the container to the device.

41. Aspect according to the aspect 39 or 40, the second type coupling elements being configured to enable a magnetic type engagement of the container to the coupling portion of the device.

42. Aspect according to the aspect 39 or 40 or 41, the second type coupling elements of the coupling portion and of the container comprising at least one respective magnet.

43. Aspect according to one of the preceding aspects, the coupling portion and the container comprising a respective first type coupling element and a respective second type coupling element, in the coupled configuration the first type coupling elements being coupled to each other, and the second type coupling elements being coupled to each other.

44. Aspect according to the aspect 43, the coupling portion and the container providing that the respective first type coupling element and the respective second type coupling element are defined at or in proximity of their opposite ends.

45. Aspect according to one of the preceding aspects, the device having a volume less than 400,000 or 200,000 m$^3$, particularly less than 175,000 m$^3$, preferably less than 150,000 m$^3$.

46. Aspect according to one of the preceding aspects, the device having a volume comprised between 20,000 mm$^3$ and 200,000 m$^3$, optionally comprised between 50,000 mm$^3$ and 200,000 m$^3$, particularly comprised between 75,000 mm$^3$ and 175,000 m$^3$.

47. Aspect according to one of the preceding aspects, the device having a volume comprised between 90,000 mm$^3$ and 150,000 m$^3$.

48. Aspect according to one of the preceding aspects, the volume of the device being defined by the box body (volume of the probe).

49. Use of the device according to anyone of the aspects from 1 to 48 and/or one of the claims of device for measuring a blood parameter, preferably correlated to the presence or concentration of oxygen in blood.

50. Use according to the aspect 49, the use does not provide any initial calibration of the device.

51. Use according to the aspect 49 or 50, the use being performed in a blood extracorporeal circuit.

52. Use according to the aspect 49 or 50 or 51, the container being placed along the blood extracorporeal circuit, the blood being contained and/or flowing inside of the container.

53. Apparatus comprising:
a device according to one of the aspects from 1 to 48 and/or to one of the claims of device,
a medical machine, for example a heart-lung machine or an extracorporeal membrane oxygenation machine (ECMO),
a user interface such as a displaying means, operatively connected or connectable to the device and configured to make available said at least one value of said blood parameter.

54. Aspect according to the aspect 53, the user interface being part of or associated or associable to the medical machine.

55. Aspect according to the aspect 53 or 54, the user interface comprising a display means, such as a screen.

56. Apparatus comprising:
a device according to one of the aspects from 1 to 48 and/or to one of the claims of device,
a medical machine, for example a heart-lung machine or an extracorporeal membrane oxygenation machine (ECMO),
a display means, such as a screen, operatively connected or connectable to the device and configured to display said at least one value of said blood parameter.

57. Aspect according to the aspect 56, the display means being part of, or associated or associable to the medical machine.

58. Aspect according to the aspects from 53 to 57, the apparatus or the machine comprising a blood extracorporeal circuit configured to circulate blood, the photosensitive element being placed along the blood extracorporeal circuit and, in operative conditions of the apparatus, being in contact with blood.

59. Method of measuring a blood parameter, preferably correlated to the presence or concentration of oxygen in blood, comprising the steps of:
exciting a photosensitive element in contact with blood by a series of excitation pulses, the blood circulating in a blood extracorporeal circuit,
dimming or terminating the excitation step between consecutive pulses of the series of excitation pulses,
detecting a plurality of light responses of the photosensitive element corresponding to the series of excitation pulses, the light responses providing respective luminescence decay curves,
analyzing the plurality of luminescence decay curves, said step providing to analyze each luminescence decay curve at least two time windows,
detecting one or more light response analog information regarding the decay of the luminescence curve at each time window.

60. Aspect according to the aspect 59, the method further comprising the steps of:
converting the light response analog information, detected at least two time windows for each light response, into light response digital data,
processing said light response digital data and the actual temperature value of blood taking into account a plurality of data of previous measures of said blood parameter performed during previous training,
determining, as a result of the processing step, at least one value of said blood parameter.

61. Aspect according to the aspect 59 or 60, the method comprising the step of predisposing a device according to anyone of the aspects from 1 to 48 and/or to one of the claims of device.

62. Aspect according to the aspect 59 or 60 or 61, the method being performed by a device according to one of the aspects from 1 to 48 and/or to one of the claims of device.

63. Aspect according to one of the aspects from 59 to 62, the method being for measuring the partial pressure of oxygen in blood, said parameter being the partial pressure of oxygen in blood.

64. Aspect according to the aspects from 59 to 63, the method comprising the step of detecting the actual temperature value of blood.

65. Aspect according to the aspects from 59 to 64, wherein.
the photosensitive element is provided with a determined chemical composition,
the step of processing said light response digital data and the actual temperature value of blood taking into account a plurality of data of previous measures of said blood parameter performed during previous training by taking into account a plurality of data of previous measures of said blood parameter performed during previous training carried out by using a plurality of photosensitive elements provided with the same chemical composition.

66. Aspect according to one of the aspects from 59 to 65, the step of determining, as result of the processing step, at least one value of said blood parameter comprising:
  determining, based on said light response digital data, a value of said parameter at the actual temperature of blood,
  determining, based on said light response digital data, a value of said parameter at a reference temperature of blood, for example at 37° C.

67. Aspect according to one of the aspects from 59 to 66, wherein:
  the method comprises the steps of predisposing a device according to one of the aspects from 1 to 48 and/or to one of the claims of device,
  the step of exciting the photosensitive element is performed by the excitation member of the device,
  the method is devoid of a step of calibrating the device between the step of predisposing the device and the step of exciting the photosensitive element.

68. Aspect according to one of the aspects from 60 to 67, wherein the step of processing said light response digital data and the actual temperature value of blood by taking into account a plurality of data of previous measures of said blood parameter is performed by a program code based on machine learning and deriving from previous training.

69. Aspect according to one of the aspects from 60 to 68, wherein the step of processing said light response digital data and the actual temperature value of blood by taking into account a plurality of data of previous measures of said blood parameter is carried out by an algorithm, preferably the algorithm being derived from previous training.

70. Aspect according to the aspect 69, wherein the algorithm deriving from previous training used in the processing step is based on learning, preferably on machine learning, the training and therefore the learning being performed before using the device, preferably during a plurality of training periods.

71. Aspect according to one of the aspects from 60 to 70, wherein the step of processing said light response digital data and the actual temperature value of blood by taking into account a plurality of data of previous measures of said blood parameter comprises one or more of the following steps:
  analyzing said light response digital data and said actual temperature value of blood by a matrix mathematical model, and/or
  fitting said light response digital data and said actual temperature value of blood to the plurality of data of previous measures.

72. Aspect according to one of the aspects from 59 to 71, wherein the method comprises, before the excitation step, the following steps:
  predisposing a device according to anyone of the aspects from 1 to 48 and/or to one of the claims of device,
  coupling the container to the coupling portion of the device.

73. Aspect according to the aspect 72, said coupling step comprising the steps of:
  coupling the container to the device by first coupling elements (first type coupling elements),
  coupling the container to the device by second coupling elements (second type coupling elements).

74. Aspect according to the aspect 73, the steps of coupling by first coupling elements and by second coupling elements being performed at respective opposite ends of the coupling portion and of the container.

75. Aspect according to the aspect 73 or 74, the step of coupling the container to the device by first coupling elements being performed before the step of coupling the container to the device by second coupling elements.

76. Aspect according to the aspect 73 or 74 or 75, the step of coupling the container to the device by first coupling elements, providing to insert a tab or hook of the coupling portion into a slit of the tubular element.

77. Aspect according to one of the aspects from 73 to 76, the step of coupling the container to the device by second coupling elements providing to magnetically couple the coupling portion to the tubular element.

78. Aspect according to one of the aspects from 59 to 77, wherein blood is contained and/or circulates in a container, for example a tubular element.

79. Aspect according to anyone of the preceding aspects, the time windows being temporally equidistant from each other.

80. Aspect according to anyone of the preceding aspects, consecutive time windows being temporally equidistant from each other.

81. Aspect according to anyone of the preceding aspects, all the time windows having a same duration.

81-bis. Aspect according to anyone of the aspects from 1 to 80, wherein the time windows have a duration different from each other.

81-tris. Aspect according to the aspect 81-bis, wherein at least one or only one time window has a duration less than the duration of the other time windows, said at least one or only one time window corresponding to a minimum, particularly to a local minimum, of the luminescence decay curve.

82. Aspect according to anyone of the preceding aspects, the time windows being in a number at least equal to three or four or five.

83. Aspect according to anyone of the preceding aspects, the container being of a disposable type.

84. Aspect according to anyone of the preceding aspects, the photosensitive element being of disposable type.

85. Aspect according to anyone of the preceding aspects, the device being of an autonomous (stand-alone) type.

86. Aspect according to anyone of the preceding aspects, wherein the analysis of each said luminescence decay curve is an analysis in the time domain.

87. Aspect according to anyone of the preceding aspects, wherein the analysis of each said luminescence decay curve is not an analysis in the phase domain.

88. Aspect according to anyone of the preceding aspects, wherein the calibration of the device occurs during the learning.

89. Aspect according to one of the preceding aspects, the learning being performed by the method according to one of the aspects from 91 to 110.

90. Aspect according to the aspect 89, wherein the learning is performed in laboratory by a laboratory set-up.

91. Machine learning method comprising the steps of:
  predisposing a set-up comprising:
    a blood extracorporeal circuit in which blood can circulate,
    a plurality of probes and a plurality of containers, probes and containers being structured to be coupled, each container being placed along said blood extracorporeal circuit so that blood can flow inside of it,
  acquiring data from measures of at least one parameter of blood circulating in the blood extracorporeal circuit, the measures being performed by said probes, preferably, the parameter being correlated to the presence or concentration of oxygen in blood,
creating a set of data comprising the acquired data,
subdividing the set of data in one or more groups,
leaning based on one or more of said groups, the learning step comprising the development of one or more models of neural network,
evaluating said one or more models, the evaluating step comprising selecting a model among said one or more models,
verifying said model.

92. Machine learning method comprising the steps of:
predisposing a set-up comprising:
   a blood extracorporeal circuit in which blood can circulate,
   a reservoir containing blood, for example a blood bag, in fluid communication with said blood extracorporeal circuit,
   a circulation member apt to move blood in said circuit,
   a plurality of devices for measuring a blood parameter, each device being associated to a respective container, each container being placed along said blood extracorporeal circuit so that blood can flow inside of it,
   a data collector, such as a multiplexer, connected to said plurality of devices in order to collect data from said devices,
   a thermometer apt to measure the temperature of blood circulating in the blood extracorporeal circuit,
acquiring data from measures of at least one parameter of blood circulating in the blood extracorporeal circuit, the measures being performed by said devices, preferably the parameter being correlated to the presence or concentration of oxygen in blood, the acquisition step comprising acquiring light response digital data regarding the luminescence curves,
collecting data by said data collector,
creating a set of data comprising acquired data,
subdividing the set of data in one or more groups,
learning based on one or more of said groups, the learning step comprising the development of one or more models of neural network,
evaluating said one or more models, the evaluation step comprising selecting a model of neural network among said one or more models,
verifying said model of neural networks.

93. Aspect according to the aspect 91 or 92, wherein the probes are probes to be trained.

94. Aspect according to the aspect 92 or 93, the set-up further comprising a blood preparation circuit along which the extracorporeal blood flows, the blood preparation circuit being configured to prepare extracorporeal blood at desired conditions, for example in terms of presence of gas in blood or saturation of blood.

95. Aspect according to the aspect 92 or 93 or 94, wherein the blood extracorporeal circuit is a main blood circuit.

96. Aspect according to the aspect 94 or 95, wherein the extracorporeal blood prepared in the blood preparation circuit is destined to flow in the main blood circuit.

97. Aspect according to one of the aspects from 91 to 96, wherein the step of acquiring data from measures of at least one parameter of blood circulating in the blood extracorporeal circuit is repeated for a plurality of learning periods.

98. Aspect according to one of the aspects from 92 to 97, wherein:
the blood extracorporeal circuit comprises a blood draw point,
the set-up comprises a reference blood analyzer configured to perform measures of a reference value of said parameter,
the method comprises the steps of:
   drawing blood at said blood draw point,
   measuring, by the reference blood analyzer, at least one reference value of said parameter,
   associating the digital data of one or more luminescence curves to said reference value of said parameter.

99. Aspect according to the aspect 98, the method comprising the step of getting information from the step of associating the digital data of one or more luminescence curves to said reference value of said parameter, the learning step using said information.

100. Aspect according to one of the aspects from 91 to 99, wherein the step of acquiring data comprises performing a plurality of iterations of a measure cycle, the measure cycle measuring said blood parameter, the parameter being preferably correlated to the presence or concentration of oxygen in blood.

101. Aspect according to one the aspects from 91 to 100, wherein the step of verifying the model comprises performing a plurality of iterations of a measure cycle, the measure cycle measuring said blood parameter, the parameter being preferably correlated to the presence or concentration of oxygen in blood.

102. Aspect according to the aspect 100 or 101, wherein the iterations of a measure cycle are performed with varying conditions, for example at different temperatures of blood and/or at different values of said blood parameter.

103. Aspect according to the aspects from 91 to 102, wherein the method comprises translating the learning deriving from the model of neural network in an algorithm.

104. Aspect according to one of the aspects from 91 to 103, wherein the machine learning method comprises the step of developing an algorithm to be implemented in the device according to one of the aspects from 1 to 48 and/or to one of the claims of device.

105. Aspect according to one of the aspects from 91 to 104, the machine learning method being destined to develop an algorithm to be implemented in the code or machine language of the control unit of the device according to one of the aspects from 1 to 48 and/or to one of the claims of device, for example in code C.

106. Aspect according to one of the aspects from 91 to 105, wherein the model of neural network is a feed-forward model of neural network.

107. Aspect according to one of the aspects from 91 to 106, wherein the model of neural network is of a multilayer type.

108. Aspect according to one of the aspects from 91 to 107, wherein the model of neural network is of a multilayer perceptron type.

109. Aspect according to one of the aspects from 91 to 108, wherein the model of neural network comprises at least three layers, among which an output layer.

110. Aspect according to the aspect 109, wherein the output layer provides two neurons, each neuron providing a respective output datum, in other words:
the value of said parameter at the actual temperature of blood, and
the value of said parameter at a reference temperature of blood, for example at 37° C.

111. Aspect according to one of the preceding aspects, wherein said parameter is one among: partial pressure of oxygen in blood, partial pressure of carbon dioxide in blood, pH of blood.

112. Aspect according to one of the preceding aspects, wherein said parameter is the partial pressure of oxygen of blood.

113. Aspect according to one of the preceding aspects, wherein each light response is a light emission.

114. Aspect according to one of the preceding aspects, wherein the light emission occurs at the end of an excitation pulse.

115. Aspect according to one of the preceding aspects, wherein the photosensitive element comprises a photosensitive substance.

116. Aspect according to one of the preceding aspects, wherein the device comprises an optical interface comprising a portion or an at least partially transparent optical interface component, the photosensitive element being associated to the portion or the at least partially transparent component.

117. Aspect according to one of the preceding aspects, wherein the device comprises an at least partially transparent optical interface component, the photosensitive element being associated to said optical interface component.

118. Aspect according to the aspect 116 or 117, the photosensitive element being deposited on said optical interface component.

119. Aspect according to the aspect 116 or 117 or 118, the photosensitive element being deposited on an at least partially transparent surface of said optical interface component, said surface being destined to come in contact, in use, with blood.

120. Aspect according to one of the aspects from 116 to 119, the optical interface component being made of plastic material.

121. Aspect according to one of the aspects from 116 to 120, the optical interface component being made of an at least partially transparent material.

122. Aspect according to one of the aspects from 116 to 121, wherein the transparency is both at the emission wavelengths of the photosensitive element and at the wavelengths of the excitation pulses which the photosensitive element is subjected to.

123. Aspect according to one of the aspects from 116 to 122, the optical interface component being configured to associate the photosensitive element to the container.

124. Aspect according to one of the aspects from 116 to 123, the container comprising a housing, the optical interface component being housed in the housing.

125. Aspect according to the aspect 124, the housing being through and being configured to enable, in use, a contact between the photosensitive element and blood.

126. Aspect according to the aspect 124 or 125, wherein the container is a tubular element provided with a mantle, the housing developing through the mantle.

Conventions and Definitions

It is observed that in the following detailed description corresponding parts are indicated by the same numeral references. The figures could illustrate the object of the invention by not-to-scale representations; therefore, parts and components illustrated in the attached figures and regarding the object of the invention could only refer to schematic representations. In the context of the present disclosure, the use of terms such as "on", "upper", "at the top", "under", "lower", "at the bottom", "sideways", "lateral", "laterally", "internal", "internally", "external", "externally", "horizontal", "horizontally", "vertical", "vertically", "front", "frontally", "rear", "rearward", "right", "left", similar terms and corresponding variants, save for specific different indications, refers to at least one spatial orientation which the object of the invention can take in condition of use. Save for different specific indications, the terms "condition" or "configuration" can be interchangeably used in the context of the present disclosure. Expressions such as "upstream", "downstream" and similar or derived expressions, refer to the arrangement of elements with respect to the advancement direction of fluid in a circuit or along one branch thereof.

In the context of the present disclosure, one or more of the following definitions and conventions can be applied, when required and unless otherwise noted:

"parameter correlated to the presence or concentration of oxygen in blood" means a parameter or magnitude directly or indirectly correlated to the presence or concentration of oxygen in blood. For example, the partial pressure of oxygen ($pO_2$) in blood is a parameter directly correlated to the presence or concentration of oxygen in blood, "luminescence curve" means a curve wherein the light intensity, emitted by a photosensitive element as a consequence of a light excitation received by an excitation member, is expressed as a function of time (see FIGS. 11 and 12); the luminescence curve has an initial portion wherein the light intensity increases due to the light excitation of a photosensitive element, until it reaches a peak, after that, due to the end of the light excitation, the light intensity decreases as a function of time (luminescence decay portion of the luminescence curve), "luminescence decay curve" means the decay portion of a luminescence curve (see FIG. 8), the light intensity is preferably a luminescence or photoluminescence intensity, the light intensity can be expressed by an arbitrary or officially recognized unit of measure; therefore, in the diagrams of FIGS. 8, 11 and 12, the light intensity, indicated in the ordinate by the reference "OI", is not indicated by a specific unit of measure, while with reference to the time, indicated on the abscissa by the reference "t", the unit of measure used is the one of seconds, in the order of magnitude of microseconds [µs], the "light response" provides light emission (luminescence), "light response analog information" means one or more continuously detectable (analogically) information or data or parameters; an example of light response analog information is the light intensity of the luminescence decay curve, which continuously varies with time, "light response digital data", known also as "luminescence digital data", means digital data regarding the light response or luminescence curve, particularly regarding the decay portion of the luminescence curve, "clinical use" of the device or of the probe means, save for otherwise indicated, the operative conditions of the previously trained device or probe, "housed" means at least partially housed, preferably completely housed, inside of the component providing the housing, the excitation of the photosensitive element is preferably a photoexcitation, i.e. it provides the determination of an excited state in the photosensitive element by the absorption of photons by this latter, the luminescence is preferably photoluminescence; i.e. it provides the light emission from the photosensitive element due to the absorption of photons.

Control Unit

The herein described and claimed device comprises at least one control unit capable of controlling/directing/managing the operations/steps performed by the device itself during its use. The control unit is substantially a control and/or processing unit configured to supervise, in condition of use, the operations/steps implemented by the device and to process data and/or the information associated to such operations. In the same way, the herein described and claimed method of measuring a parameter of blood can use at least one control unit capable of controlling/directing/managing the steps of method. In the following, for the sake of clarity, the control and/or processing unit is indicated by the term "control unit".

The control unit can be a single control unit or include a plurality of distinct control units, according to design choices and operative requirements. Preferably, the control unit is housed in the device.

The term "control unit" indicates an electronic component which can comprise at least one among: a digital processor (CPU), a microprocessor, an analog circuit, or a combination of one or more digital processors with one or more analog circuits. The control unit can be "configured" and/or "programmed" to perform some operations/steps: this can be done with any means and/or modes enabling to configure and/or program the control unit.

Structural and operative aspects regarding the control unit are examined in the detailed description, where the control unit is indicated by the numeral reference 5.

BRIEF DESCRIPTION OF THE DRAWINGS

In order to better comprehend the invention and appreciating the advantages, some embodiments thereof will be described in the following in an exemplifying and non-limiting way with reference to the attached figures, wherein.

DETAILED DESCRIPTION OF EMBODIMENTS OF THE INVENTION

Figure 1:
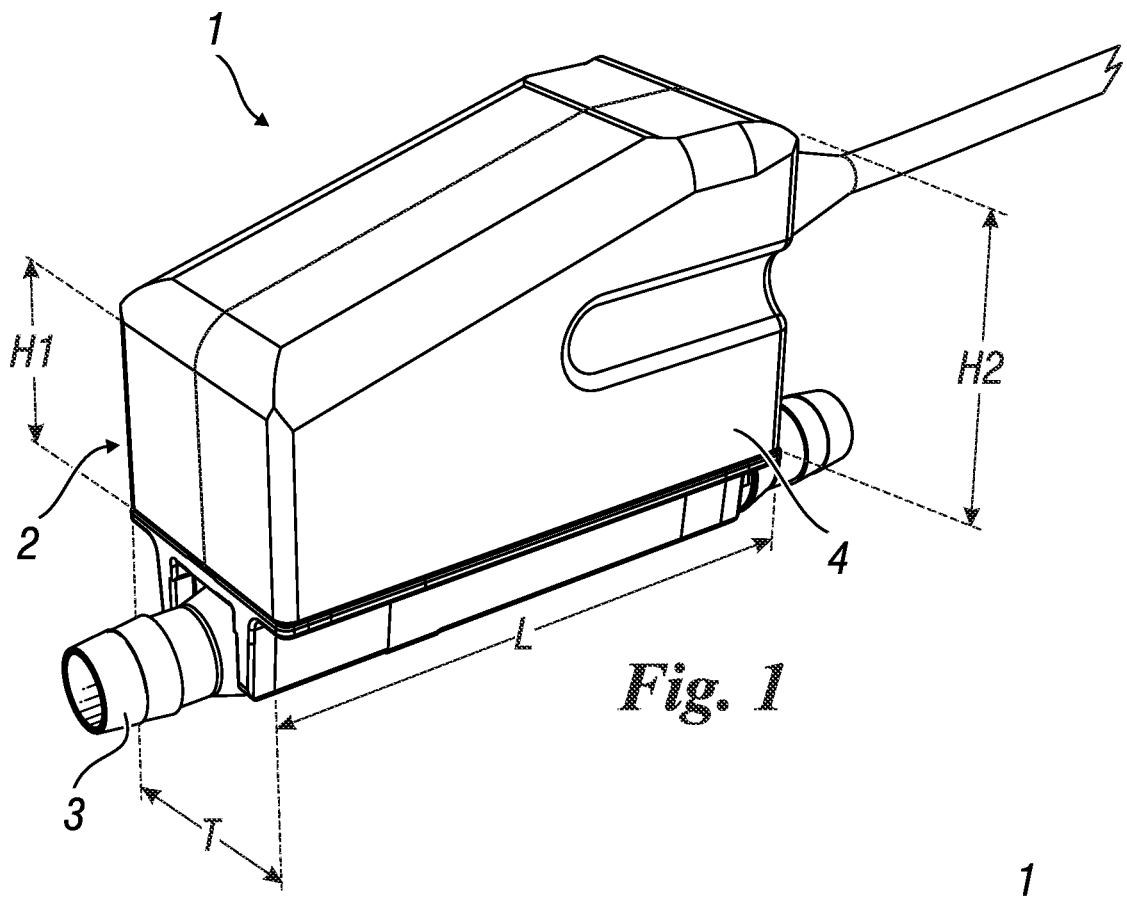
FIG. 1 illustrates a device for measuring a blood parameter according to an embodiment of the invention, wherein the probe and the cuvette are in a coupled configuration.
Figure 2:
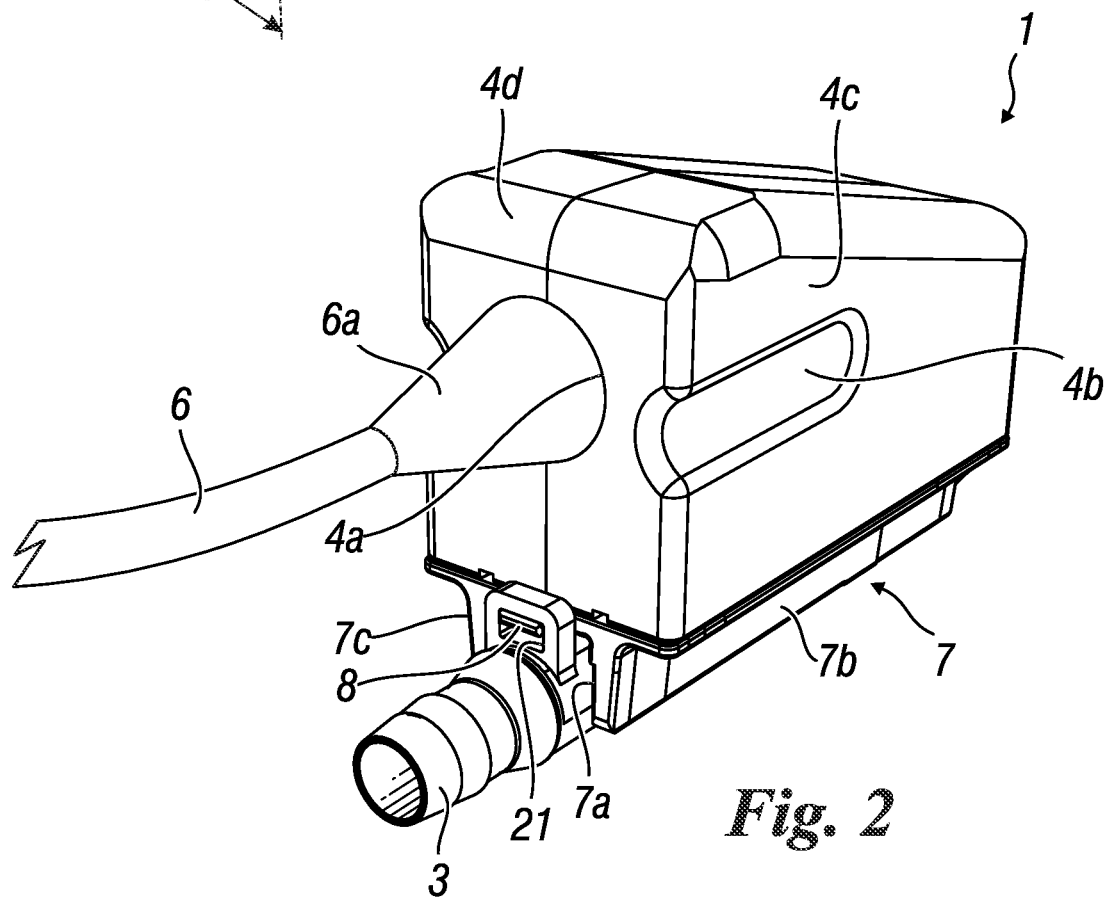
FIG. 2 illustrates a rear view of the device of FIG. 1.
Figure 3:
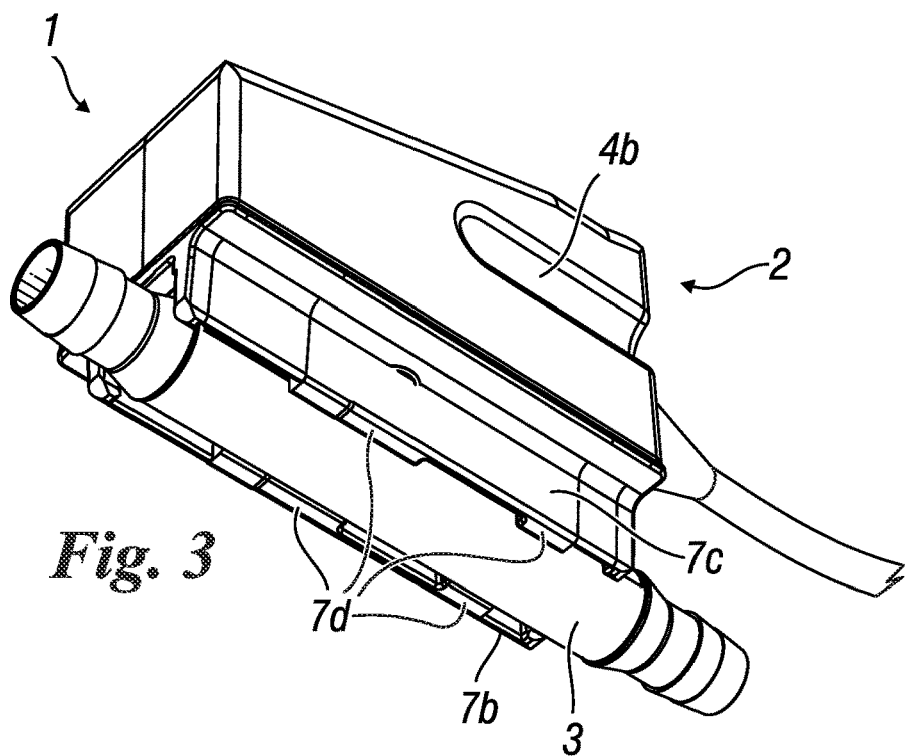
FIG. 3 illustrates a bottom view of the device of FIG. 1.

Device for Measuring a Parameter of Blood

A device according to the invention is generally indicated in the figures by the numeral reference 1. The device 1 is configured to measure a blood parameter. Preferably, the parameter is correlated to the presence or concentration of oxygen in blood. Possible examples of such parameters are: the partial pressure of oxygen ($pO_2$) of blood, the partial pressure of carbon dioxide ($pCO_2$) of blood or the pH of blood.

The device 1 substantially comprises a probe 2, a container 3 for blood and an optical interface portion 17. The optical interface portion 17 is associated to the container 3; particularly, it is at least partially inserted in the container 3 in order to be, in use, at least partially in contact with blood. The optical interface portion 17 comprises an optical interface component 18 comprising a photosensitive element 18', preferably in the form of a photosensitive substance. Preferably, the optical interface component 18, which is made of a transparent plastic material, provides that on its face destined to come in contact with blood, a photosensitive substance 18' will be deposited. Possible methods of depositing the photosensitive substance 18' are: spin coating, sputtering, tampography, or serigraphy. The probe 2 and container 3 with the associated optical interface component 18 are designed and structured to be coupled and operatively interact with each other, as it is specifically described in the following. The container 3 and the optical interface component 18, since in use they are contact with blood, form the disposable elements of the device 1, while the probe 2 can be reused for performing further measures of the parameter.

The probe 2 comprises a box body 4. The box body 4 has an internal volume in which the components which will be described in the following are housed, among which a control unit 5. Moreover, the box body 4 has an opening 4a apt to enable the connection by a cable 6; the cable 6 enables to transmit processed digital data from the control unit 5, to a medical machine and/or a display means. Further, the cable 6 enables to electrically supply the probe 2. As illustrated in the attached figures, the cable 6 can have a stress-relief element 6a apt to prevent or minimize stresses at the portion of the cable 6 passing through the box body 4. The box body 4 has at least one handle portion apt to enable to easily grip and handle the probe 2; as illustrated in the attached figures, the handle portion can be in the shape of a pair of grooves 4b defined on opposite sides of the box body 4. The bod body 4 has a small size providing compactness to the probe and also to the device 1. From the geometrical point of view, the box body 4 has a length L, a width T and a height H; preferably, the width T is less than the length L and height H. Preferably, the box body 4 has a shape so that its interior houses the required components of the probe with the smallest possible volume. As illustrated in the attached figures, the height H can vary along the length L; therefore, the box body 4 can have the smallest height H1 and the greatest height H2, which can be defined at respective opposite ends with respect to the length L of the box body 4. The length L, measured along the prevalent development direction of the container 4, can be comprised between 40 and 80 mm. The width T, measured orthogonally to the length L, can be comprised between 15 and 50 mm. The height H, measured orthogonally to the length L and the width T, can be comprised between 30 and 80 mm. By way of a non-limiting example, it is noted that, in a preferred embodiment, the length L can be equal to 65 mm, the greatest height H2 can be equal to 58 mm, and the width L can be equal to 35 mm. The volume of the box body 4 defines the volume of the probe 2; the volume of the probe 2 can be comprised between the volumes determinable from the limits of the above cited dimensional ranges. Specifically, in possible embodiments, the volume of the probe 2 can be comprised between 20,000 mm$^3$ and 400,000 m$^3$, optionally comprised between 50,000 mm$^3$ and 200,000 m$^3$, particularly comprised between mm$^3$ and 175,000 m$^3$, still more particularly comprised between 90,000 mm$^3$ and 150,000 m$^3$. Moreover, it is noted that the box body 4 can be assemblable; particularly, it can comprise two portions 4c, 4d which, in the operative conditions of the device, are assembled with each other. As illustrated in the attached figures, the assemblable portions can be half-shells 4c, 4d; preferably, the half-shells are substantially symmetrical to each other.

The probe 2 comprises a coupling portion 7 associated to the box body 4. With reference to the orientation of the device 1 illustrated in the attached figures, the coupling portion 7 is associated to the box body 4 at its lower portion. The coupling portion 7 can develop parallel to the length L of the box body 4 between two opposite longitudinal ends of the bod body 4. The coupling portion 7 can be integral with the box body 4. The coupling portion 7 comprises a housing 7a provided with a volume sized to house a blood container 3, particularly a cuvette. The housing 7a can be in the shape of a groove developing along the development longitudinal direction of the coupling portion 7. As illustrated in the attached figures, the coupling portion 7 can be in the shape of a skirt emerging from a lower portion of the box body in order to delimit the housing 7a; the skirt has opposite walls 7b, 7c, the housing 7a being defined between them. Since the measure is of an optical type, it is advantageous to shield as much as possible the optically sensible zone from components of external light; to this purpose, the walls 7b, 7c are configured to shield the light and prevent reflections or direct light from possibly biasing the measure. Each wall 7b, 7c can be integral with the respective semi-shell 4c, 4d. Moreover, each wall 7b, 7c can comprise one or more structural elements 7d, which can be in the shape of recesses and/or ribs, configured to enable a univocal coupling between the container 3 and probe 2 and, in addition or as an alternative, lighten (by the recesses) or reinforce (by the ribs) the wall which they are defined on. Preferably, the walls 7b, 7c provide recesses/ribs 7d having the double function of lightening/reinforcing the wall which they are defined on and to enable the univocal coupling between the probe 2 and a determined container 3, which in turn can have corresponding structural elements 3d. This enables to exchange the containers 3, such as cuvettes, between arterial or venous probes; in other words, this enables the herein described probe (arterial probe) 2 to be univocally coupled to an arterial cuvette 3 thanks to the corresponding recesses/ribs 3d that this latter is provided with, consequently preventing a venous cuvette from being coupled to the arterial probe 2.

The coupling portion 7 comprises at least one coupling element 8, 9 enabling the device 1 to take a coupled configuration in which the container 3 is coupled to the probe 2 (illustrated in FIGS. 1, 2, 3 and 6) and a decoupled configuration in which the container 3 is disengaged from the probe 2. The blood parameter is measured in the coupled configuration, in which the container 3 is housed into the housing 7a. As illustrated in the attached figures, the coupling portion 7 can comprise at least one first type coupling element 8 and at least one second type coupling element 9. The first and second type coupling elements 8, 9 can be arranged at respective longitudinal opposite ends of the coupling portion 7. The first and second type coupling elements 8, 9 are configured to be coupled to corresponding coupling elements of the container 3, which will be described in the following. Providing coupling elements 8, 9 of two different types makes coupling the probe 2 to the container 3 more safe and stable. According to a preferred embodiment, the first type coupling element 8 enables the mechanical coupling between the probe 2 and the container 3, while the second type coupling element 9 enables the magnetic coupling between the probe 2 and container 3. The first type coupling element 8 can comprise, for example, a tab or a hook. In the embodiment illustrated in the attached figures, the first type coupling element 8 of the coupling portion 7 comprises a hook and the second type coupling element 9 of the coupling portion 7 comprises a magnet.

Moreover, the probe 2 comprises an optoelectronic unit which will be described.

The probe 2 comprises an excitation member 10, which is housed inside of the box body 4. The excitation member 10 is configured to excite a photosensitive element associated to the container 3 by a series or train of excitation pulses; the pulses are of an optical type. As it will be described in the following, in operative conditions of the device 1, the photosensitive element responds at the end of each excitation pulse with a light emission (luminescence) which decays with time when the excitation pulse ends. The excitation member is illustrated in the attached figures as an excitation LED 10, in other words a LED configured to excite the luminescence of the photosensitive element. Preferably, the optical pulse used for "querying" the photosensitive element is by a very high power LED 10 and is generated by a gate driver capable of supplying high powers for very short time intervals without generating electronic noise which would disturb the digital analog converter provided by the control unit 5 of the probe. It is noted that, in alternative embodiments, the excitation member 10 can be a laser. The emission wavelength of the LED which is a function of the type of photosensitive substance 18', is 390 nm in the herein described preferred embodiment. With photosensitive substances 18' apt to enable to measure other parameters, the wavelength can vary between 350 and 700 nm.

Figure 4:
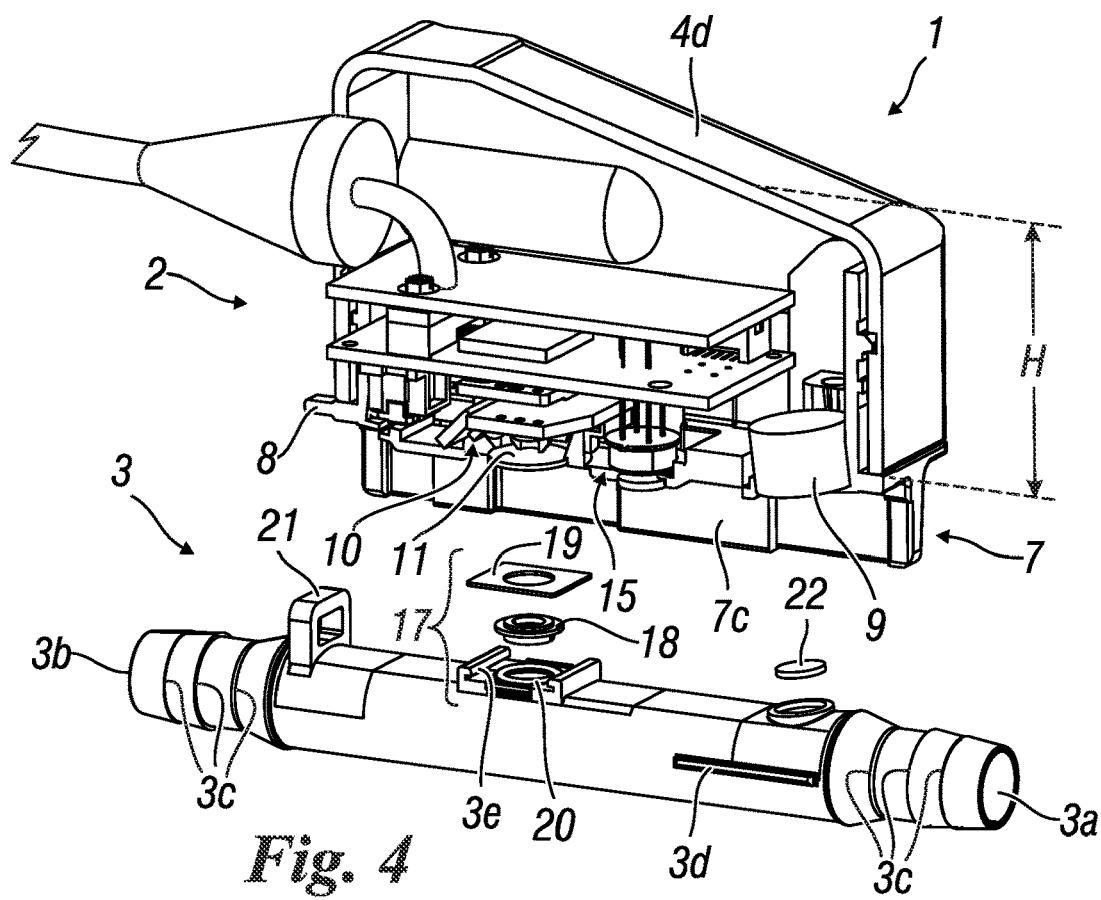
FIG. 4 illustrates the probe and the cuvette of the device of FIG. 1 in a decoupled configuration; the box body of the device is open in order to show the components housed inside of it and the components associated to the cuvette are illustrated in an exploded view.
Figure 5:
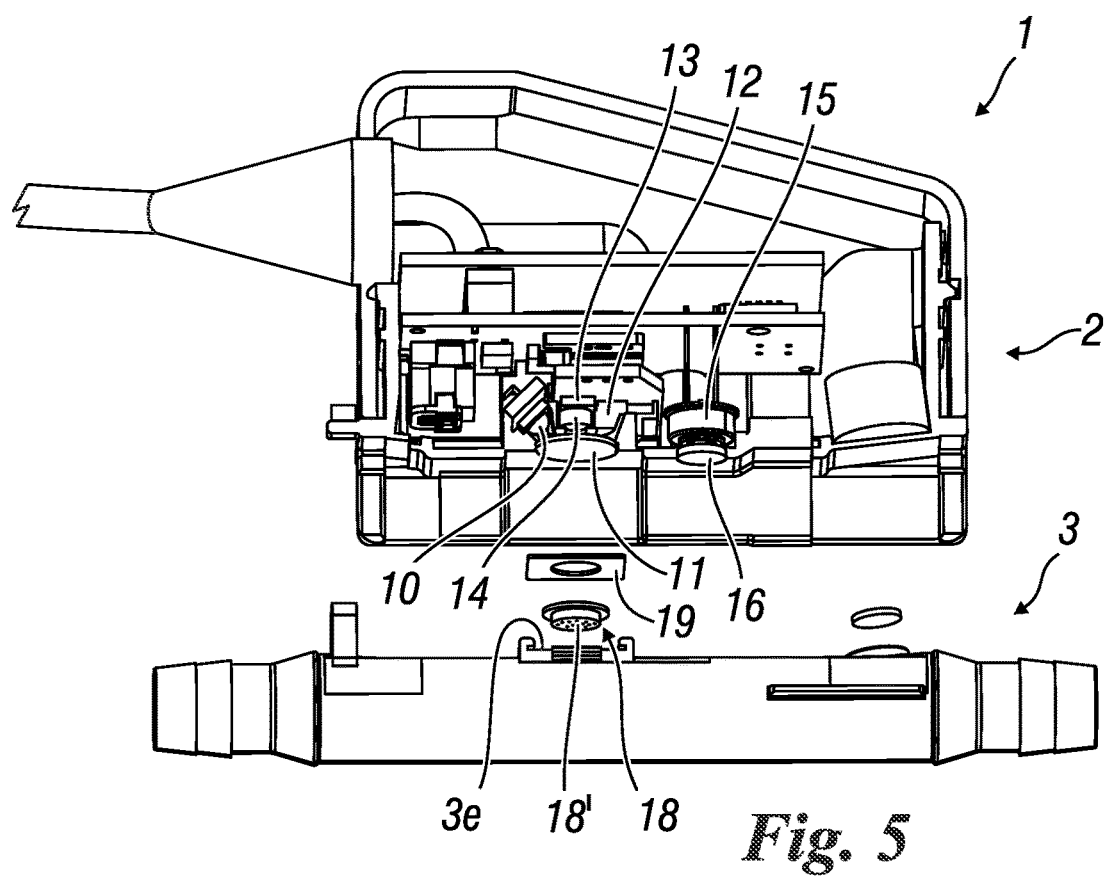
FIG. 5 illustrates a partial bottom view of the device of FIG. 4.
Figure 6:
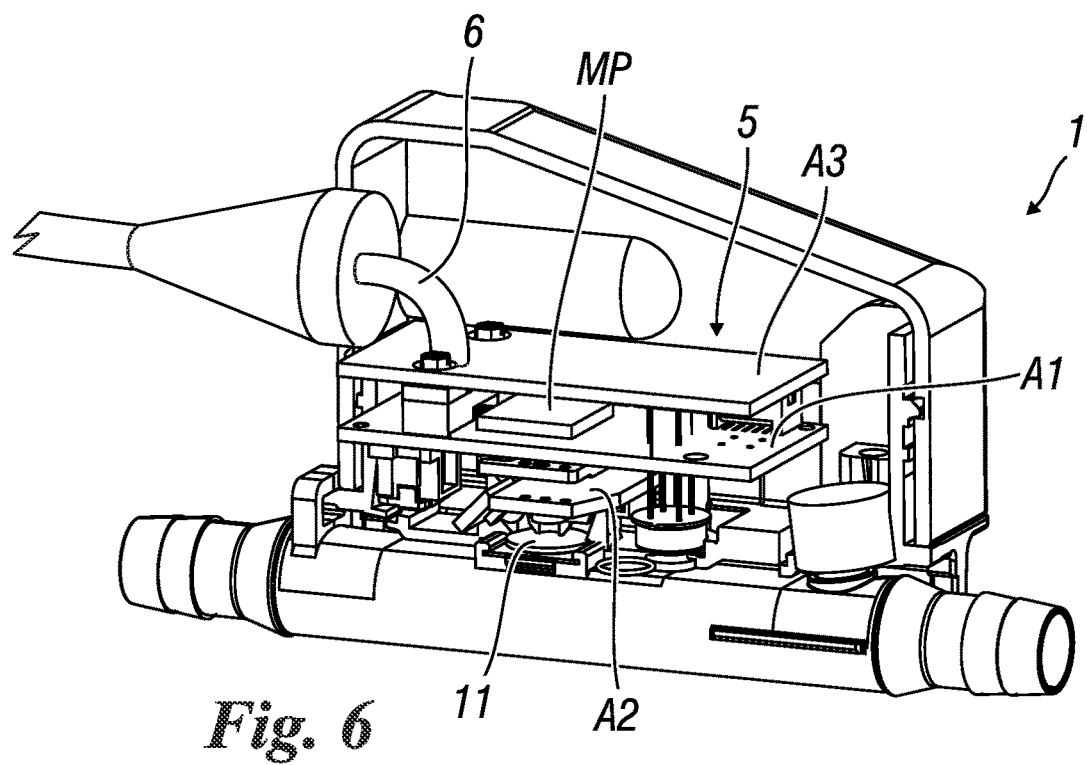
FIG. 6 illustrates the device of FIG. 1 in operative conditions, wherein the cuvette is engaged with the probe; the box body of the device is open in order to show the components housed inside of it.

Preferably, the probe 2 comprises a protection window 11 arranged between the excitation member 10, the photodetector 13 which will be described in the following, and the photosensitive element. FIGS. 4, 5 and 6 illustrate that the protection window 11 can be provided at the lower portion of the box body 4 in proximity of the coupling portion 7; such placement enables the protection window 11 to face, in the coupled configuration of the device 1, the photosensitive element of the container 3. The protection window 11 is apt to protect all the components housed in the box body 4.

In addition, the probe 2 can comprise a shield element 12 configured to suppress the light radiation of the excitation member 10. Preferably, the shield element 12 is housed inside of the box body 4.

Further, the probe 2 comprises a photodetector 13 housed inside of the box body 4. The photodetector 13 is configured to detect, in operative conditions of the device, a plurality of light responses of the photosensitive element corresponding to the series of excitation pulses emitted from the excitation member 10. More particularly, the photodetector 13 is apt to detect a determined wavelength of the incident electromagnetic wave and to transform the absorption of photons in a current electric signal by exploiting the photoconductive effect. The photodetector 13 is configured to detect frequencies comprised between 300 nm and 1600 nm; in function of the frequencies that the photodetector 13 detects, it is possible to measure a determined blood parameter. As illustrated in the attached figures, the photodetector can be a photodiode 13 and in the preferred embodiment, it can detect frequencies comprised between 400 and 1100 nm. The photodiode 13 can be of the silicon PIN (Si PIN) type, silicon avalanche (Si APDs) type, InGaAs avalanche (InGaAS APDs) type, silicon (Si) type, or a combination of these.

Moreover, the probe 2 comprises a pass-band filter 14 interposed between the protection window 11 and the photodetector 13 (see FIG. 5). The pass-band filter 14 is configured to enable frequencies to pass through inside of a determined interval (pass-band) and to attenuate the frequencies outside of it. The pass-band corresponds to the frequencies which the photodetector 13 is configured to detect. The pass-band filter 14 is housed inside of the box body 4. As illustrated in FIG. 5, the pass-band filter 14 can be housed inside of a hollow portion of the shield element 12. In the preferred embodiment, the pass-band filter 14 is inserted in an optical trap configured to shield the photodiode 13 from the direct light of the excitation member 10 and to receive/collect, for filtering it, only the luminescence at an optimal incidence angle. In the preferred embodiment, the optical trap is an element preferably made of a black color plastic material and having a cylindrical shape with a small diameter and a length of few millimeters. Such optical trap enables only the light entering parallel to its axis to reach, without being attenuated by reflections on its walls, the pass-band filter 14 so that the light perpendicularly strikes the filter. In this optical condition, the pass-band filter 14 optimally performs its filtering action by enabling only the fluorescence light radiation and not the excitation one to reach the photodetector 13.

Moreover, the probe 2 comprises a temperature sensor 15 housed inside of the box body 4 and configured to detect the temperature of blood. Specifically, the temperature sensor 15 is configured to detect the blood temperature inside of the container 4. Preferably, the temperature sensor 15 is arranged in proximity of the coupling portion 7 in order to enable to easily detect the temperature of blood housed in the container 4. Still more particularly, the temperature sensor 15 is arranged in proximity of the coupling portion 7 in order to face the container 3 in the coupled configuration of the device 1. Preferably, the temperature sensor 15 is an infrared temperature sensor.

The probe 2 can comprise a protection window 16 in order to protect the temperature sensor The protection window 16 is apt to protect the temperature sensor 15 from the electromagnetic waves at frequencies different from the frequencies which the temperature sensor 15 can detect. In the embodiment in which the temperature sensor 15 is of an infrared type, the protection window 16 can be made of a material configured to allow radiations at the infrared frequency to pass through; for example, the protection window 16 can be made of zinc sulphide (ZnS).

Further, the probe 2 comprises a control unit 5, which is housed inside of the box body 4. The control unit 5 enables the probe 2 and therefore the device 1 to measure the parameter without requiring an initial calibration. Further, the control unit 5 preferably enables the device 1 to perform the measure without interacting with any processing or computing unit outside of the device 1; processing information and data for measuring the blood parameter is therefore performed autonomously by the probe 2. Consequently, it is not required to provide a database outside of the probe 2; the probe 2 provides, inside of the box body 2, all the components apt to perform the desired measure. The probe 2 is capable of, by means of the control unit 5, performing the measure of the parameter based on a plurality of data of previous measures of the blood parameter performed during a previous training. This is made possible because the control unit can be provided with a coded computing model. Training is preferably carried out in laboratory prior to the supply of the probe 2 (e.g. by the supplier of the probe 2 on the basis of requests from the user of the probe 2) and therefore is not to be carried out by the user of the probe 2, who consequently has an immediately ready for use instrument. As it will be detailed in the following, the previous training determines a learning, particularly a machine learning, which the control unit takes into account when measuring the parameter for a clinical use.

The probe 2 and also the device 1 are particularly adapted to be used in emergency conditions because they do not need an initial calibration. Examples of emergency conditions are the ones requiring a treatment by an extra-corporeal membrane oxygenator (ECMO), in other words of a cardiocirculatory assistance, for example in patients affected by cardiac arrest or lung trauma in the untreatable most acute phases such as the Covid-19 disease (COronaVIrus Disease 19 caused by virus SARS-CoV-2, indicated in the following simply by "Covid").

From the point of view of the implementable operations, the control unit 5 is configured to: analyze the luminescence decay curves at a plurality of time windows t1-tN, process information and/or data regarding the analysis of luminescence curves, and determine (measuring), as a result of the processing operation, at least one value of the blood parameter. As it will be more specifically understood in the following, the plurality of time windows t1-tN can comprise a number N of time windows optimized based on the previous training.

Particularly, the control unit 5 is preferably configured to perform the following operations:

receiving, for each at least two time windows t1-tN for analyzing each luminescence curve, one or more light response analog information regarding the luminescence decay curve, converting the light response analog information, detected at least two windows t1-tN for each light response, into light response digital data, processing the light response digital data and the actual temperature value of blood by taking into account a plurality of data of previous measures of the blood parameter performed during previous training, determining, as a result of the processing operation, at least one value of the blood parameter.

Substantially, the control unit 5 receives at the input the actual temperature value of blood and the light response analog information from the photosensitive element of the container 3, it processes them based on the previous training and measures the value of the parameter. The actual temperature value of blood is measured by the temperature sensor 15 which detects the blood temperature in the container 3.

Referring to the operation of determining at least one value of the blood parameter, it provides to determine two values of the same blood parameter, each value at a respective temperature. Substantially:

a value of the parameter at the actual temperature of blood, in other words at the temperature of blood contained or flowing in the container 3, and a value of the parameter at a reference temperature of blood, which can be of 37° C., are determined.

This enables, from one side, to measure the blood parameter at the actual temperature of blood circulating in the extracorporeal circuit and, on the other side, to report the performed measure at the temperature of 37° C., which is the reference body temperature relevant to the health staff.

The analysis of the luminescence decay curves destined to measure the blood parameter is performed in the time domain, at a plurality of time windows t1-tN; by not analyzing the luminescence decay curves in the frequency domain, the invention enables a measure of the parameter performed by the probe 2 without having the typical inconveniences of the analysis in the frequency domain of the luminescence curve. Now it is necessary to give a short description for briefly explaining the principles of the analysis of a luminescence curve in a frequency domain. When a luminescence curve is analyzed in the frequency domain, a photosensitive element is excited by a sinusoidally modulated light; consequently, the photosensitive element responds with a luminescence intensity having also a sinusoidal trend but offset from the excitation signal. The modulation frequency f is kept constant so that the tangent of the offset angle $\phi$) is directly correlated to the decay time $\tau$ by the following formula: $\tan \phi = 2\pi * f * \tau$. The decay time $\tau$ is in turn correlated to the concentration of oxygen by the Stern-Volmer equation. The disadvantages of the analysis in the frequency domain of the luminescence curves are consequently tied to the fact that are required relatively high signals and that the duration is an indirectly measured parameter; therefore, the heterogeneity of the duration cannot be directly detected. The invention, by analyzing the luminescence decay curve in the time domain, allows to overcome such disadvantages.

Figure 8:
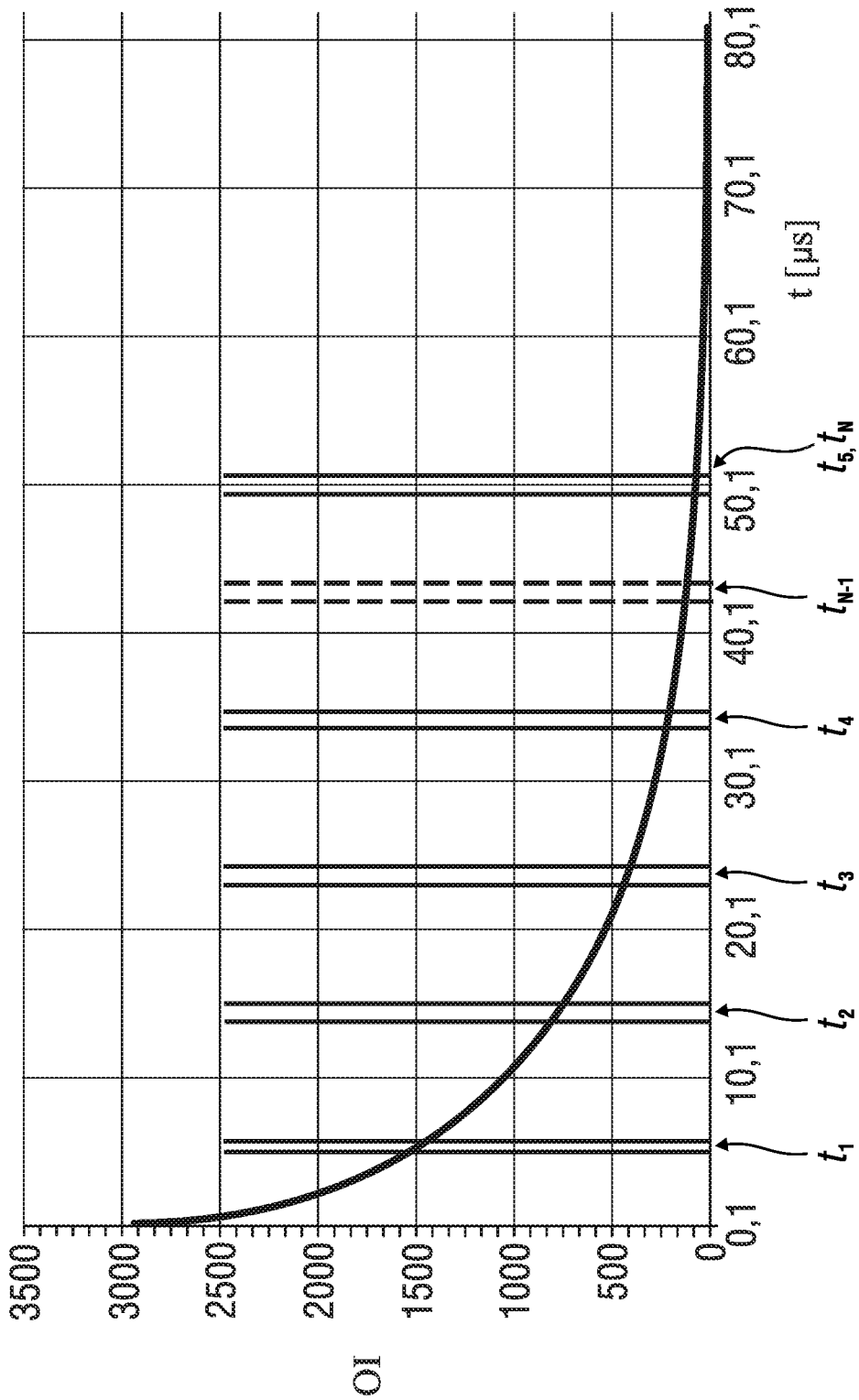
FIG. 8 illustrates a diagram of a luminescence decay curve, which shows the trend of the light intensity of the photosensitive element associated to the cuvette of the device of FIG. 1, emitted due to excitation, as a function of time; the luminescence decay curve is analyzed at a plurality of time windows.

The control unit 5 is configured to manage the operations/steps of exciting the photosensitive element and of analyzing the luminescence decay curve according to the following modes. In use, the control unit 5 controls the emission of pulses from the excitation member, and particularly the emission timeliness of the series of excitation pulses. Moreover, it is noted that the plurality of analyzed time windows t1-tN according to the invention comprise at least two time windows t1-t2, optionally at least three time windows t1, t2, t3, or at least four time windows t1, t2, t3, t4. The time windows t1-tN can be in a maximum number of N, without any particular limit except the one tied to the set-up used for analyzing such curves. FIG. 8 illustrates a luminescence decay curve analyzed at five time windows. Still in FIG. 8, the last time window tN and the last but one time window tN−1, which is dashed, indicate generally that more time windows can be present than the ones shown in the figure. Particularly, the number N of time windows t1-tN can be selected and optimized based on the quantity of information one wants to obtain and/or based on the "zones" of the decay curve which one wants to analyze. Relevant zones of the decay curve to be analyzed are the ones having a greater variation based on the measure conditions, in other words the ones in which the light intensity OI decays faster with time.

In turn, the time distance of the time windows t1-tN can be function of the one or of the zones of the decay curve one wants to analyze. The term distance of the time windows t1-tN means the time distance between consecutive time windows. To this matter, it is necessary to observe that the time windows t1-tN can be temporally distanced in order to cover the luminescence decay curve at least in the zones with a greater variation of the curve itself. Preferably, the time windows t1-tN can be temporally equidistant from each other; particularly, the consecutive time windows t1-tN can be temporally equidistant from each other. Preferably, each time window has a duration comprised between about 3 μs and about 100 μs, preferably between about 6 μs and about 80 μs. The time windows t1-tN have a duration different from each other. Particularly, a time window can have a shorter duration than the other time windows. It is understood that a different number N, distance, duration and other characteristics of the time windows t1-tN can be changed in order to enable an optimal analysis of the luminescence decay curve.

It is also noted that the control unit 5, based on the type of training which it is subjected to, can process digital data according to one between at least two modes: a first processing mode providing to analyze the light response digital data and the actual temperature value of blood by a matrix mathematical model and a second processing mode providing to fit the light response digital data and the actual temperature value of blood, preferably by a best-fitting technique, to the plurality of data of previous measures. Evidently, it is possible to provide also combinations of such two modes or further modes. The first and second processing modes respectively correspond to a first and second learning modes of the probe, which will be described in the following and are illustrative modes among the possible training modes which can be provided. The first learning mode provides a machine learning of the probe and is based on neural networks, while the second learning mode is based on the rapid lifetime determination of a luminescence decay time (known also as method RLD) method and on a best-fitting technique.

From the point of view of the components, the control unit 5 can comprise at least one microprocessor MP and an analog-digital converter (ADC). The microprocessor MP can determine and supervise the course of the above mentioned operations and the analog-digital converter performs the conversion operation of the analog information into digital data. An analog-digital converter apt to such application is an ultra-fast analog-digital converter (ultra-fast ADC), the use therefore enables to increase the acquisition speed, in other words the speed by which the analog-digital converter is capable of acquiring the luminescence/fluorescence optical signal. Preferably, the analog-digital converter is configured to acquire the luminescence/fluorescence optical signal at a speed such to detect the signal in the decay time of the luminescence/fluorescence curve even though it is less than 6 µs; this advantageously enables to analyze the curve, formed by sufficient acquisition points, also in case of a so fast decay. Particularly, in the performed tests, an ultra-fast analog-digital converter was used in the mode "interleave", by which it is possible to obtain an acquisition speed from 5 MSPS (Mega Samples Per Second) to 18 MSPS with a resolution from 6 bit to 12 bit. Using the analog-digital converter in the interleave mode advantageously enables to reduce the required components, consequently enabling a miniaturization which was unobtainable until a few years ago. The microprocessor makes the beforehand cited computing model, obtained from and developed by a previous training, to be implemented in a program code, preferably in code C. Moreover, in tests, an ARM (Advanced RISC Machine) architecture microprocessor was used with optimal results in terms of digital data processing.

Further, the control unit 5 can comprise one or more assemblies of printed circuits (PCA). Substantially, the printed circuit assembly is a board populated by, in other words on which are placed, selected electronic components enabling the assembly to perform the function/s which is designated for. As illustrated in the attached figures (see in particular FIG. 6), the control unit 5 can comprise a printed circuit assembly A1 for the microprocessor MP, a printed circuit assembly A2 for the analog part of the photodetector 13 and a printed circuit assembly A3 for electrically powering the probe 2.

After having specifically described the probe 2 and its components, now it is described the container 3 referring particularly to the characteristics enabling it to functionally and structurally interact with the probe 2 for measuring the blood parameter. The container 3 is apt to contain blood; particularly, the container 3 is apt to enable blood to flow inside of it in operative conditions of the device 1. In order to enable blood to flow inside of the container, the container is preferably a tubular element 3 provided with an internal volume in which blood can flow in the operative conditions of the device 1. Illustratively, the following description refers to the container as the tubular element 3; it is understood that the container can have different shapes, however being still capable of performing the functions which it was designed for.

The tubular element 3 has a blood inlet 3a and a blood outlet 3b, which fluidically communicate with the internal volume and, respectively enable blood to enter and exit the internal volume of the tubular element 3. As illustrated in FIG. 4, the inlet 3a and the outlet 3b can be defined at opposite ends of the tubular element 3; it is understood that the inlet 3a and outlet 3b can be exchanged with respect to what is illustrated in FIG. 4. The tubular element is illustrated in the attached figures as a cuvette 3 provided with an inlet 3a and an outlet 3b opposite to each other and a circular passage cross-section. The tubular element 3 can be installed in a blood extracorporeal circuit and enables blood to flow from the blood inlet 3a and outlet 3b. In order to enable to be installed in a blood extracorporeal circuit, the opposite ends of the tubular element 3 can have respective connection arrangements 3c, for example in the shape of barbs. The connection arrangements 3c enable an effective connection of the ends of the tubular element 3 to respective conduits of the blood extracorporeal circuit. Preferably, the tubular element 3 has a rectilinear longitudinal development defined along a prevalent development direction.

The tubular element 3 comprises one or more structural elements 3d configured to be coupled to corresponding structural elements 7d of the beforehand described walls 7b, 7c. The tubular element 3 in Figures from 1 to 6 has a pair of structural elements 3d opposite with respect to its diameter. Each structural element 3d is configured to enable the univocal coupling between the arterial probe 2 and the arterial tubular element (cuvette) 3. Each structural element 3d can be a rib; to this matter, see FIG. 4.

The tubular element 3 comprises an optical interface portion 17 configured to optically interface with the probe 2. The optical portion 17 comprises a housing 3e. Preferably, the housing 3e is defined at a central portion of the tubular element 3, interposed between the opposite ends of the tubular element 3. In the embodiment of the device 1 illustrated in the attached figures, the housing 3e has a through hole developing through the mantle of the tubular element 3.

Moreover, the device 1 comprises a photosensitive element 18'. Preferably, the photosensitive element 18' is associated to the tubular element 3. The tubular element 3 and the photosensitive element 18' make up the disposable elements of the device 1. The photosensitive element 18' is substantially a sensor spot (an oxygen sensor spot if the measure is of a parameter correlated to the presence or concentration of oxygen in blood) and, in operative conditions, is in contact with blood in order to enable to measure a blood parameter. The photosensitive element 18' is configured to respond, at the end of an excitation which is subjected to when it is in contact with blood, with a light response; the light response comprises a luminescence decay curve. Preferably, the photosensitive element 18' is housed in a corresponding housing 3e of the tubular element 3. In the preferred embodiment, wherein the housing has a through hole 3e, the optical interface component 18 is engaged into the through hole 3e so that the photosensitive element 18' is in contact with blood, in conditions of use. With reference to the optical interface component 18, it is noted that it is transparent in the preferred embodiment, and particularly transparent both to wavelengths of the excitation pulses and to the wavelengths of the light emission of the photosensitive element 18 due to the housed pulses. From the point of view of the material of the optical interface component 18, it can be made of plastic material or another material. Particularly, the optical interface component 18 can be made of any material, such as a glass material, which makes it transparent.

In order to enable to engage, particularly to fix, the photosensitive element 18' to the tubular element 3, it is provided a stop 19, such as a clip. As illustrated in the attached figures, the stop 19 is apt to be arranged above the photosensitive element 18' in order to block it at the housing 3e. The stop 19 can have a hollow portion apt to enable the optical interaction between the photosensitive element 18' and probe 2. The stop 19 or clip can be made of metal material. Moreover, a gasket 20, such as an O-ring, disposed between the photosensitive element 18' and a portion of the tubular element 3 defined at the housing 3e, can be provided. The gasket 20 is apt to ensure the fluid tightness in order to prevent, in use, blood from seeping between the tubular element 3 and the photosensitive element 18'. The gasket 20 is arranged around the through hole of the housing 3e.

In the preferred embodiment, the photosensitive element is a photosensitive substance 18' deposited on a surface of the optical interface component 18 destined to come in contact, in use, with blood; in FIG. 5, such surface is a lower surface of the optical interface component 18 which, when the optical interface component 18 is housed in the housing 3e, faces an internal volume of the tubular element 3. The photosensitive substance 18' will be more specifically described in the following.

The photosensitive substance 18' has a determined chemical composition, responsible for its photosensitivity. The chemical composition of the photosensitive substance 18' determines which parameter the device 1 can measure. Preferably, the photosensitive substance 18' is a fluorophore. Possible fluorophores which can be selected based on the blood parameter to be measured are specifically described in an exemplifying and non-limiting way.

For measuring the partial pressure of oxygen, the fluorophore can be selected among those having a lifetime of the luminescence by an order of magnitude of microseconds and a high quantum yield; for example, preferably the fluorophore can be selected among the benzoporphyrins. Particularly, Pt(II) or Pd(II) benzoporphyrins can be selected since they have a strong phosphorescence at room temperature, an absorption molar coefficient from moderate to high and a large distance between the excitation wavelength and the emission one of the luminescence; moreover, the duration of the luminescence is rather long (from microseconds to milliseconds). Particular benzoporphyrins which were tested and that can be advantageously used for detecting the partial pressure of oxygen in blood are Pt(II) tetraphenyl porphyrin (aka TPP) or Pt(II)-meso-tetra(pentafluorophenyl)porphyrin. Such benzoporphyrins enable to have a lifetime of the luminescence rather long (in the order of some μs) which allows a better analysis of the luminescence curve, particularly with reference to its decay portion.

For measuring another blood parameter, whose concentration acts on the lifetime of the luminescence, a photosensitive substance 18' can be used, such as a fluorophore, having different chemical composition than the one of the above described fluorophores apt to measure the partial pressure of oxygen. For example, in order to configure the device to measure pH or partial pressure of carbon dioxide of blood, it can be used a specific fluorophore as 8-hydroxypyrene-1,3,6-trisulfonic acid trisodium salt or HPTS, pHrodo Green dye, 1,4-diketopyrrolo-[3,4-c]pyrroles or DPPs, or boron-dipyrromethene or BODIPY.

Even though the photosensitive substance 18' can be specifically selected and consequently can vary in order to adapt the device 1 to a determined parameter to be measured, the components of the optoelectronic unit for exciting the photosensitive substance 18' (excitation member 10 and components interacting with it) and for measuring (temperature sensor 15) remain unchanged, so that remain unchanged the method of collecting data sets, the structure of the neural network and its training. The photosensitive substance 18' selected for measuring a determined parameter, which is used in operative conditions of the device 1 (clinical use), has the same chemical composition as the plurality of photosensitive substances 18' used in the corresponding plurality of devices employed in the training and learning steps of the probe. In other words, during the training step, photosensitive substances 18' of the same type are used, in other words provided with the same chemical composition, as the one of the photosensitive substance or substances 18' which will be used in the operative conditions of the device 1. This enables the control unit 5 to be suitably trained, before clinically using the device 1, to recognize the value of the parameter to be measured without requiring an initial calibration of the device 1. The training modes are explained in the following.

With reference to the step of predisposing the tubular element 3 to be coupled to the probe, it is noted that the element provides at least one coupling element 21, 22 configured to be coupled to the coupling element 8, 9 of the probe 2. In the embodiment illustrated in the attached figures, at the opposite ends of the tubular element 3 respective coupling elements 21, 22 are defined. Particularly, at one end at least one first type coupling element 21 is defined and at the opposite end at least one second type coupling element 22 is defined. The first and second type coupling elements 21, 22 are configured to be coupled to the corresponding beforehand described coupling elements 8, 9 of the probe 2. The first type coupling element 21 enables the mechanical coupling of the probe 2 to the tubular element 3, while the second type coupling element 22 enables the magnetic coupling of the probe 2 to the tubular element 3. In the embodiment illustrated in the attached figure, the first type coupling element of the tubular element 3 provides a slit 21, the interior thereof being configured to enable the engagement with the tab or hook 8 of the probe 2, and the second type coupling element comprises a magnet 22 configured to be coupled to the magnet 9 of the probe 2.

The technical characteristics herein disclosed with reference to functions of the device 1 can be applied in the field of corresponding uses of the device 1 or steps of the method of measuring a blood parameter which will be described in the following and consequently can be used for specifying such uses and method in the attached claims.

The following will describe two modes which were tested to train the probe 2 with reference to the measure of the partial pressure of oxygen in blood; it is understood that training the probe can be performed according to a plurality of other modes and, in addition or alternatively, for a plurality of other parameters.

Machine Learning Based on Neural Networks

Learning is made by extensive laboratory ex-vivo tests, in other words performed by using prepared extracorporeal blood and by making it to circulate in a set-up 50 in which the conditions of blood and of the environment are modified to simulate substantially all the possible conditions which the device 1, according to the invention, can be subjected to in the clinical use. The conditions which are simulated are: the temperature of blood, the flow rate of blood, the room temperature, the oxygen saturation in blood, the pH, the hematocrit of blood. The following will describe the set-up 50 by which the probes for determining a machine learning laboratory model are tested and trained, then will be described the training modes. In the performed learning tests, the environmental conditions were not changed; consequently, the measures were acquired at room temperature. However, it is noted that generally it is possible to vary the room temperature; this would entail the use of the set-up 50 in a temperature chamber.

Figure 9:
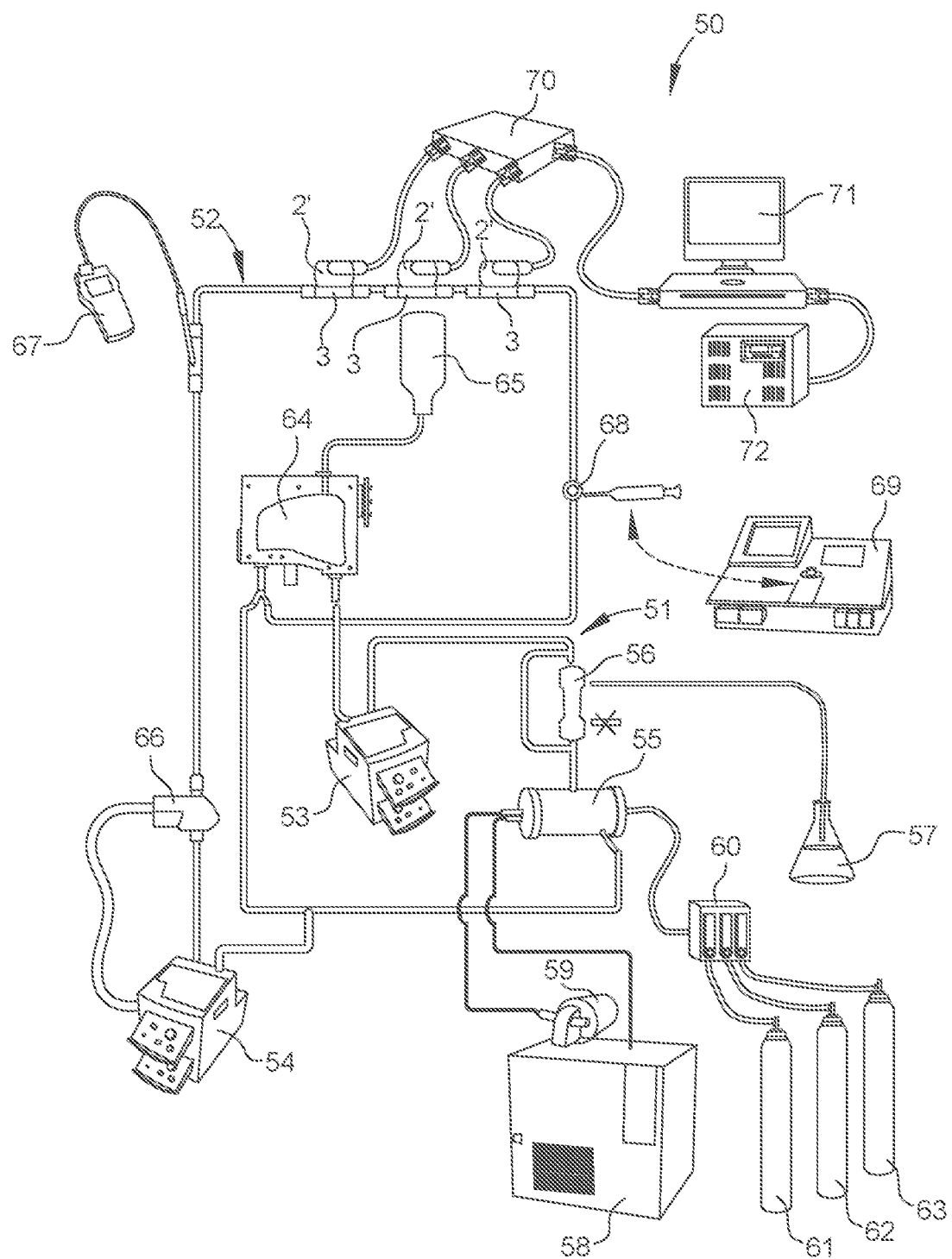
FIG. 9 illustrates a laboratory set-up destined to enable the machine learning of the devices according to the invention.

The set-up 50 is shown in FIG. 9 and comprises two circuits along which the extracorporeal blood flows. More particularly, it is provided a blood preparation circuit 51 and a main blood circuit 52 in which blood, suitably prepared by the blood preparation circuit 51, is made to circulate for performing measures of the parameter. The circuits 51, 52 are differently illustrated in FIG. 9, by respective different lines. The main blood circuit 52 is mainly illustrated in the top portion of FIG. 9 (it extends at the left in FIG. 9, to the lower portion of the figure), while the blood preparation circuit 51 is illustrated in the bottom portion of FIG. 9. In the blood preparation circuit 51 and in the main blood circuit 52 blood is made to circulate by a respective movement member 53, 54; particularly, for this purpose the set-up comprises a main impeller pump 54 for the main blood circuit 52 and a secondary impeller pump 53 for the blood preparation circuit 51.

The blood preparation circuit 51 enables to prepare blood in the desired conditions. For this purpose, the set-up comprises a blood oxygenator 55 and a plasma filter 56 arranged along the blood preparation circuit 51.

The plasma filter 56 is the component having the function of extracting plasma from blood in order to be capable of "concentrating" blood for the purpose of increasing the hematocrit value. The plasma filter 56 is connected to an extracted plasma discharge container 57, which receives plasma removed by the plasma filter 56. Removing plasma is made by a pressure gradient which establishes between the blood preparation circuit 51 and the extracted plasma discharge container 57; in order to interrupt the plasma removing step, the line connecting the plasma filter 56 to the extracted plasma discharge container 57 is closed.

With reference to the blood oxygenator 55, it is the component of the set-up 50 having, in the blood preparation circuit 51, functions equivalent to the ones of human lungs; it is configured to oxygenate the blood, remove carbon dioxide and also heat or cool blood as herein below described. For this purpose, the blood oxygenator 55 comprises a heat exchanger and is connected to a thermostatic bath 58. Moreover, the set-up 50 comprises a water pump 59 configured to circulate water between the thermostatic bath 58 and the blood oxygenator 55. The thermostatic bath 58 is configured to heat or cool water which by the water pump 59 is made to circulate in the heat exchanger integrated in the blood oxygenator 55; consequently, blood is cooled down or heated up to the desired temperature. For modifying the blood saturation conditions, and particularly the oxygen saturation conditions of blood, the blood oxygenator 55 is connected to a gas mixer 60, which in turn is connected, upstream, to an oxygen reservoir 61, a nitrogen reservoir 62 and a carbon dioxide reservoir 63. The gas mixer 60 is configured to mix in varying proportions gases from the just described three reservoirs 61, 62, 63. As illustrated in FIG. 9, the reservoirs can be in the shape of bottles 61, 62, 63 configured to supply the gas mixer 60 with a respective gas.

The blood preparation circuit 51 and the main blood circuit 52 have an element in common, consisting in a blood container 64, which in FIG. 9 is illustrated as a blood bag. The blood container 64 acts as a supply from which blood is withdrawn by the secondary impeller pump 53 and, since the blood preparation circuit is a closed circuit, blood once is suitably prepared flows back to it. The blood container 64 is connected to an isotonic solution source 65, which is configured to supply the isotonic solution. Since the isotonic solution is devoid of red cells, providing it to the blood container 64 enables to dilute the blood contained in it. The isotonic solution, known also as physiological solution, enters by gravity into the main blood circuit 52 and performs an action contrary to the one performed by the plasma filter 56. The blood container 64 enables to supply, by the main impeller pump 54, the main blood circuit 52 with blood suitably prepared by the just described blood preparation circuit 51.

Moreover, the set-up 50 provides, along the main blood circuit 52, a plurality of containers of the beforehand described type, these are therefore called in the following tubular elements 3, associated to respective probes 2' provided by the set-up 50. The tubular elements 3 coupled to the probes 2' are of a disposable type and have a respective photosensitive substance 18' (sensor spot or oxygen sensor spot) facing the blood stream flowing in the main blood circuit 52. In order to train the probes 2' to measure a specific parameter, the photosensitive substances 18' are of the same type and consequently have the same chemical composition. The probes 2' provided by the set-up 50 are optoelectronic probes configured to excite the respective photosensitive substance 18' associated to the respective tubular element and to detect the respective light response; their excitation optoelectronic unit and their components for detecting the light response are analogous to the beforehand described one. Substantially, the probes 2' of the set-up are of the beforehand described type, except for the fact they are devoid of the algorithm enabling to autonomously measure the blood parameter for the clinical use, because this algorithm is under development by the herein described training. Still more particularly, probes 2' and probes 2 distinguish for the calibration coefficients, which will be described in the following. Upon the "calibration" of such probes 2', performed by training in laboratory, the probes 2' are configured to calculate the value of the parameter by using the suitably trained neural network in all the operative conditions which could happen during the clinical use of the probe 2. It is stressed that such training/calibration is performed in laboratory, in other words before the clinical use of the probe 2. As illustrated in FIG. 9, the tubular elements 3 and the respective probes 2' can be in number equal to three; it is understood that a plurality of probes 2' and corresponding tubular elements 3 in number different from three can be provided, particularly, the number is greater than or equal to four. The number of probes 2' will increase as the number of detected "raw" data increases.

Moreover, the set-up 50 comprises, along the main blood circuit 52, a blood flowmeter 66 and a temperature detector 67; this latter acts as an instrument for verifying and reporting the temperature.

The flowmeter 66 is configured to measure the blood flow rate in the main blood circuit 52. The flowmeter 66 can measure the blood flow rate downstream the main impeller pump 54. In FIG. 9, the flowmeter is illustrated as connected to the main impeller pump 54.

The temperature detector 67 is configured to measure the blood temperature, preferably in proximity of the tubular elements 3 coupled to respective probes. In FIG. 9, the temperature detector 67 is illustrated as a digital thermometer provided with a temperature sensor dipped in blood and placed upstream and in proximity of the tubular elements 3 coupled to the probes 2'.

Moreover, the main blood circuit 52 provides a blood draw spot 68 and a reference blood analyzer 69. The blood draw spot 68 is a spot in the circuit in which an extracorporeal blood sample is drawn; the drawn sample is analyzed by the reference blood analyzer 69, which is the reference instrument which the "raw" measures (and the respective "raw" data) obtained by the plurality of probes 2' of the parameter are referred to. The reference blood analyzer 69 is a clinically accepted reference instrument and therefore it provides the measure of the parameter with the required precision. Substantially, the reference blood analyzer 69 provides a value of the parameter which is a reference value of the parameter at specific conditions (actual temperature of blood, for example, oxygenation of blood) at which the measure is performed. In the performed tests, regarding the parameter of partial pressure of oxygen in blood, the reference blood analyzer 69 measures at least the value of the partial pressure of oxygen in blood; it is understood that, when measuring another parameter such as the pH of blood or the partial pressure of carbon dioxide in blood, the reference blood analyzer 69 will be configured at least for measuring such other parameter. The reference blood analyzer illustrated in FIG. 9 is a laboratory hematochemical analyzer 69.

By the set-up 50 of FIG. 9, the beforehand indicated conditions are therefore changed, and, at each variation, it is acquired the luminescence decay curve; the so acquired curves are digitized by the components contained in the probe 2'. Consequently, the analog information detected at a plurality of time windows t1-tN of the curve for a given variation of a condition are transformed into digital data which can be processed. The value of the parameter corresponding to the condition, which is varied, the analog information and the relative digital data are associated to the value of the parameter (in the performed tests, $pO_2$), measured by the reference blood analyzer 69. By an extensive simulation of each possible condition with can occur in the clinical use, it is possible to obtain thousands of data associated to digitized parameter/luminescence curves for each of the conditions set in laboratory, which comprise all the ones for which one wants the probe 2 to measure the parameter of them.

Moreover, the set-up comprises a data collector 70 and a computer 71. The data collector 70 is connected to the plurality of probes 2' in order to collect data from the probes 2'; the collected data are digital data regarding the analysis of the luminescence decay curves at a plurality of time windows t1-tN. As illustrated in FIG. 9, the data collector 70 can have a plurality of inputs in number equal to the one of the probes 2' of the set-up 50 and at least one output for the connection to the computer 71 in order to collect the data. The data collector 70 is substantially an electronic instrument; the data collector used in the tests, shown in FIG. 9, is a multiplexer 70. After having collected the data, the data collector 70 transfers them to the computer, which in FIG. 1 is exemplified by a personal computer 71. The computer 71 collects the "raw" data from the probes 2' for all the operative conditions which one wants to verify; these "raw" data are a set of data used for training the neural network.

Moreover, the set-up can comprise an external datastore 72, connected to the computer 71 and configured to store the data housed from the computer 71. Substantially, the external datastore is an electronic datastore 72, which can be remote, for saving data.

Having described the set-up 50 which enables the training, now the machine learning method based on neural networks will be discussed. As beforehand said, it is provided a data acquisition step which provides to acquire luminescence decay curves at different values of the parameter to be measured (see FIG. 11 with reference to the parameter $pO_2$) and a plurality of data regarding the variation of the operative conditions in which the measures are done. Substantially, the data acquisition step provides to vary the operative range of the probe 2' with reference to the blood temperature, concentration of oxygen in blood (consequently the variation of $pO_2$), the pH of blood, the concentration of carbon dioxide in blood (therefore the variation of $pCO_2$). Such conditions are varied by the beforehand described blood preparation circuit 51. In the acquisition step, it is possible to use a number of probes 2' according to what was beforehand described; particularly, in order to have a greater variability of the measures, the number of the used probes 2' can be greater than four. The probes 2' must be already calibrated according to the temperature. The calibration of the probes 2' provides that the probes 2' are already connected to a circuit inside which a liquid at a controlled temperature flows; by acquiring the temperature by the temperature sensor 15 integrated in the probes 2' and by comparing the measure with the one read by the temperature verifying instrument 67 placed in the circuit 52, it is possible to calculate and provide the probes 2' with a correction equation enabling the probes 2' to perform a temperature measure aligned with the one of the temperature reference instrument 67 used during the calibration.

After acquiring the data, the learning method comprises the generation of sets of data; such step provides to balance the data acquired in the different conditions with a plurality of measures in all the conditions, relative to the luminescence decay curves as a function of the values of $pO_2$, the temperature, the pH and $pCO_2$ of blood; these latter values are measured by the reference blood analyzer 69, while the measures and the analysis of the luminescence decay curve are performed by the probes 2'. The acquired set of data, on which the machine learning is based, must be sufficiently large in terms of luminescence curves/values of the parameter, with an order of magnitude of tenths of thousands of data; for example, it can comprise about 10,000 pairs of luminescence curves/values of the parameter. Providing a sufficiently wide set of data enables to take into account also the variability of the response to the light excitation of the photosensitive elements. For each luminescence curve, the mean values of the areas subtended by the curves at a plurality of time windows t1-tN are calculated; the areas subtended by the curve correspond to the integration of the curve. In the tests performed with reference to the measure of $pO_2$, the luminescence decay curves were analyzed at five time windows t1-t5 distributed in the time range between about 6 and 60 µs (see FIG. 8, where N=5); particularly, the used time windows t1-t5 had a duration varying between 0.5 and 2 µs. The position and the duration of the windows were evaluated by using suitable optimization algorithms. An optimization algorithm which was used is the "Powell's conjugated direction method", which is an algorithm for calculating a local minimum of a function, in order to determine duration and position of the time windows which make as small as possible the MAPE (mean absolute percentage error) of the predictions which are obtained by the model; in this case, the function analyzed by the Powell's conjugated direction method is the luminescence decay curve. The prediction, among the determined windows, of a time windows of a shorter duration enables to minimize the prediction error of the considered measure. It is understood that number N, duration, distance, and variation of the time windows t1-tN can be according to what was beforehand described. The time windows t1-tN are suitably positioned on the luminescence curve in order to obtain the best information contribution in the range of interest for the parameter to be measured, for example in the range of interest of the oxygen concentration.

Upon the generation of the data set, the data set is divided into three groups: a group of training data, a group of validation data, and a group of test data. The group of training data is the one on which the neural network is effectively trained, while the group of validation data and the group of test data are for evaluating the validity (in terms of accuracy) of the predictions the trained model will provide. Preferably, the data set is randomly divided. More particularly, the data set was divided in this way: 60% for learning, 20% for validation, and 20% for tests; the randomness is introduced by mixing the lines of the data set, for preventing the learning from being influenced by possible ordered sequences. The lines are mixed before dividing the data set.

Now, the method comprises the machine learning, wherein there is a learning step and a step of evaluating models. The learning step provides to develop different models of neural network based on the group of training data; the models can be different with reference to the evaluation of the input parameters, the variation of the time windows t1-tN, the duration and distance thereof, and the variations of the cost functions (for example the non-linear cost function or mean absolute error). The step of evaluating the models provides to evaluate the performance of the different models on the group of validation data and on the group of test data in order to determine the best; preferably, the evaluation is done on the group of test data, in other words a portion of 20% of all the initial data set. The best model can be one providing the best results on the group of training data. In order to evaluate the best model, the validity of the performed predictions from the model is evaluated by metrics; the most used are the Mean Absolute Percentage Error, and the percentage of beyond-threshold predictions, in other words with an error greater than 10%. In the performed tests, which used a very large set of data, small variations of the mathematical model did not substantially affect the validity of the predictions; this means a greater accuracy of the probe 2. The result which is considered the best is the one for which all the analyzed curves have an accuracy less than +/−10%; the less the percentage of the beyond-specification points is, the better the model will be.

Lastly, the learning method provides a verifying step or test of the selected model of neural network, in which the model is verified by new experimental data in the whole the whole measure range or field, by varying the temperature of blood and parameter to be measured (for example $pO_2$). Measure field means the range in which, in the clinical use of the probe, the parameter to be measured can vary. For the temperature, the measure field can be comprised between 15° C. and 41° C., with reference to the parameter $pO_2$, the measure field is substantially comprised between 50 mmHg and 400 mmHg. It is noted that this last range refers to $pO_2$ at the actual temperature (effective temperature) of blood; the $pO_2$ at 37° C. has a different range which cannot be defined a priori.

Figure 10A:
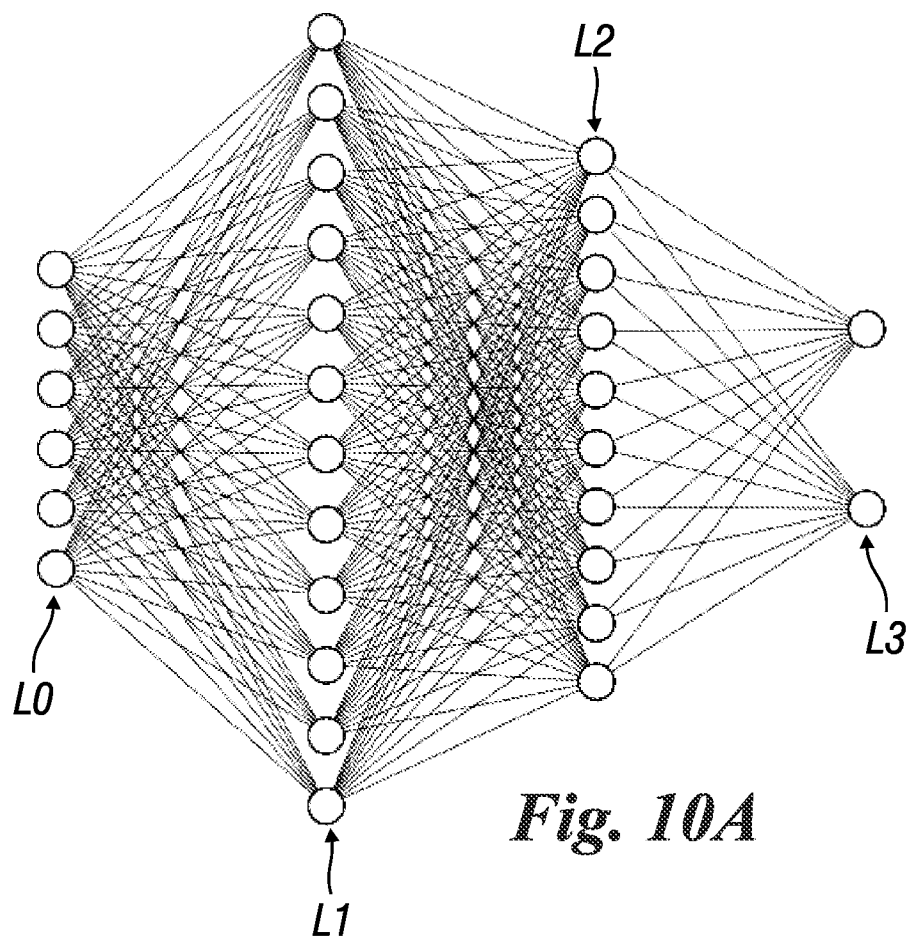
FIG. 10A illustrates in an exemplifying way, the structure of the multilayer perceptron type neural network, which is a possible structure of the neural network which can be implemented in the device according to the present invention.

In the performed test, a neural network of the multilayer perceptron (MLP) type was selected, which is shown in FIG. 10A. The multilayer perceptron type neural network is a model of artificial neural network which maps sets of input data to a set of suitable output data. Moreover, such neural network is of the feedforward type, in other words is an artificial neural network in which the connections among the nodes do not form a cycle. It is understood that, based on the previously described method, different types of machine learning neural network can be selected; in the following it is described the type of selected neural network, with reference to the tested application which provides to measure $pO_2$. Clearly, the following can be applied, once the necessary changes have been made to the measure of another blood parameter.

The neural network in FIG. 10A is an input layer or input L0 provided with six neurons, the first layer L1 completely connected by twelve neurons, a second layer L2 completely connected by ten neurons, and a third layer L3 completely connected by two neurons. The two neurons of this latter layer L3 which is the output layer, correspond to values exiting the neural network, in other words: the value of $pO_2$ at the reference temperature of blood (37° C.) and the value of $pO_2$ at the temperature of the blood sample. Remaining firm the number of neurons of the output layer L3, the other layers L0, L1, L2 can have a number of neurons and/or a number of layers different from the herein described one, in function of the particular optimization performed for the model of the selected neural network. The number of neurons for each layer can be partially tied to the computing capacity of the microprocessor MP of the control unit 5 of the probe 2'. All the neurons of the network are sigmoidal at the activation; the activation of a neuron corresponds to the moment in which the neuron activates and performs its function of transferring information (illustrated in FIG. 10C and indicated in the following as sigmoid), enabling to transmit information of the input stimulus.

The data entering the neural network will be described in the following. With reference to the example of analyzing luminescence decay curves at five time windows t1-t5, five mean values of the areas subtended by the curve are obtained; these are scaled to be amplitude normalized so that relatively very high values weigh in the neural network more than the relatively small ones and in order to obtain a more effective training of the neural network. Substantially, based on the collected learning group, the minimum and maximum values of each parameter entering the network are calculated and a normalization is performed before transferring them to the network and a denormalization is performed after obtaining the output data. The values must be scaled again before being transferred to the network in this way: normalized value=(detected value−minimum value)/(maximum value−minimum value). In the same way, the value exiting the network must be scaled again for obtaining the real value in this way: denormalized value=value*(maximum value−minimum value)+minimum value. It is required to scale again the partial pressures of oxygen between 0 and 1 because the domain of the sigmoid is between 0 and 1, therefore the output of the network will be always a number comprised in this range. Further, the values are scaled again for preventing relatively very high or very small values of the domain (axis x in FIG. 10O), for which the first derivative of the sigmoid function is almost zero, from causing difficulties/slowness to the learning; in this case, the gradient will be subjected to a very small change of slope which will cause a slow convergence towards the global minimum point. Normally, one tries to maintain the values proceeding as input between $-\sqrt{3}$ and $+\sqrt{3}$. These five scaled again values are provided to the input of the neural network; in the neural network shown in FIG. 10A, five of the six neurons therefore correspond to a respective value. The other neuron of the input layer corresponds to the value of the blood temperature, detected by the temperature detector.

Consequently, the neural network is capable, based on the provision at the input of a determined number of values calculated from a luminescence curve and of the blood temperature calculated in a tubular element placed in a blood extracorporeal circuit, of calculating at the output the value of $pO_2$ at the reference temperature of blood (37° C.) and the value of $pO_2$ at the actual temperature of blood circulating in the tubular element. Such computing, which makes possible the measure performed by the probe 2, in the neural network which is selected and tested is made as follows.

Figure 10B:
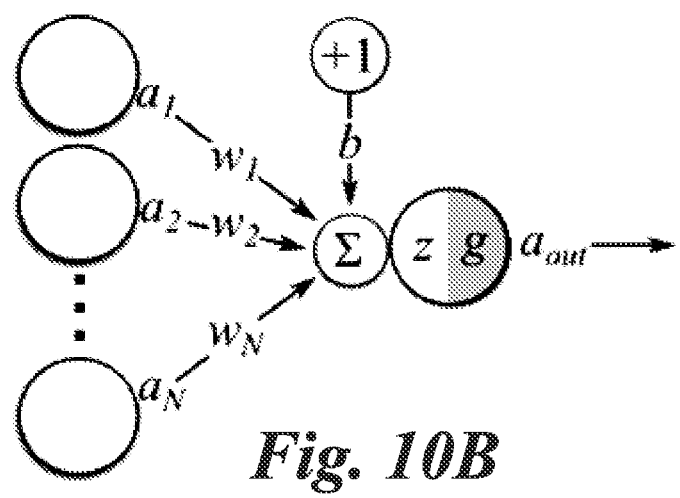
FIG. 10B illustrates a possible computing method implementable by the neural network of FIG. 10A for measuring the two values of the blood parameter exiting the neural network.

The used computing method is shown in FIG. 10B and comprises the following formulas, wherein the symbol * is the scalar product:

$$z = b + \Sigma_{i=1}^{N} ai * wi \quad \text{(formula 1)}$$

$$a_{out} = g(z) \quad \text{(formula 2)}$$

In the formula 1, it is noted that:
$w_i$=weight$_i$
$b_i$=bias$_i$
"wi" and "bi" are respectively matrixes of weights and biases; weights and biases are calibration coefficients.

With the matrixes, the computing model is a matrix mathematical model.

With reference to formula 2, it is specified that $a_{out}$ is the output of each neuron, therefore also those of the internal layers L1, L2.

More particularly:
for the first layer L1:

$$a1 = x\_input + w1 + b1$$

$$z1 = \text{sigmoid}(a1)$$

for the second layer L2:

$$a2 = z1 * w2 + b2$$

$$z2 = \text{sigmoid}(a2)$$

for the third layer L3:

$$a3 = z2 * w3 + b3$$

$$z3 = \text{sigmoid}(a3)$$

$$\text{output} = z3$$

Since two neurons are provided in the output layer L3, one of them has as output the value of $pO_2$ normalized at 37° C., while the other has as output the value of $pO_2$ at the actual/effective temperature.

This latter layer L3, which provides the output results of the neural network model, consists of two variables, in other words the value of $pO_2$ at the reference temperature of blood (37° C.) and the value of $pO_2$ at the effective temperature of blood circulating in the tubular element.

Figure 10C:
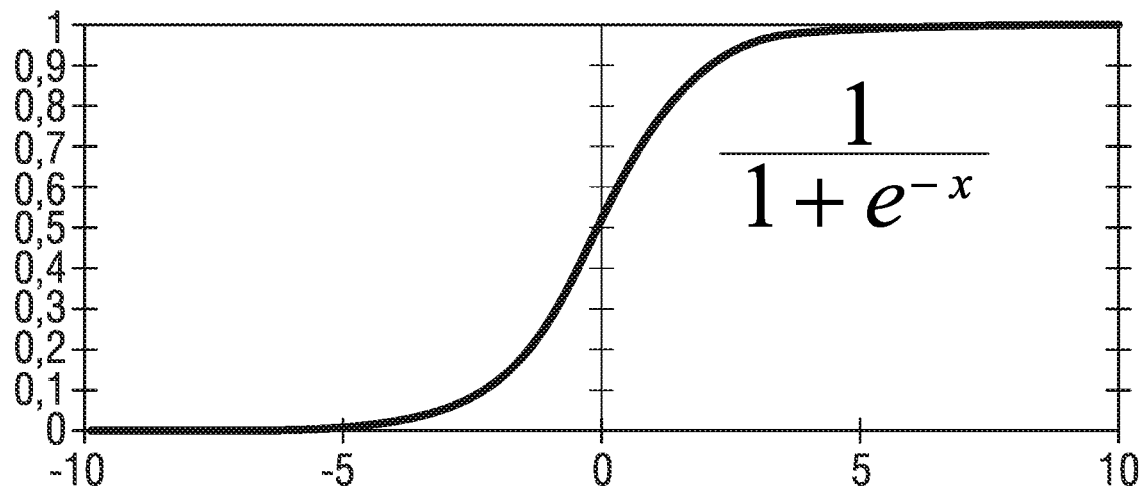
FIG. 10C shows the function for activating the neurons.

Moreover, it is noted that:
"i" is comprised between 1 and N,
"N" is the number of nodes (neurons) for each layer of the neural network,
"x_input" is the vector of the input values/parameters taken from the luminescence curve,
"a", "b", "w" are obtained by the learning step,
"g(z)" is the activation function of the neuron and is illustrated in FIG. 10C.

Some thousands of training periods were performed (1 period corresponds to a complete cycle of all the examples) with an average batch size of 4 examples for batch. In the performed tests, the learning was performed for $4*10^5$ periods and with an adaptive learning rate starting from a value of 0.001 for preventing the over-fitting. It is noted that the learning rate is one of many parameters which is set during the learning step of the neural network; it is for modifying the step of the optimizer. It was used an optimizer known as "Adam", which derived from the gradient method.

With reference to not specifically detailed aspects regarding the machine learning, it is made reference to the literature regarding the theory of the neural networks.

For each connection of the network there is a function, translated into language code C in the microprocessor MP, called sigmoid in other words a mathematical function (sublayer) connecting the neurons. The inputs of each neuron of the network are matricially multiplied by the parameters of the network, the result thereof is transferred to the sigmoid function by the hereinbefore given formulas. The result of the sigmoid function is the intermediate output of each layer, in other words the input to the neurons of the following layer.

During the learning, it is selected a non-linear cost function or target function (Mean Absolute Error) modified in order to quadratically weigh more than the examples with low $pO_2$ (which are subjected to a greater percentage error).

The final result of the neural network model is represented by a series of parameters, in other words matrixes of weights and biases $w_i$ and $b_i$. Substantially the neural network model learns, by extensive laboratory tests and measures, which are the best values of the matrixes of weights and biases $w_i$ and $b_i$ apt to provide at the output, against the input vector x_input, the two values of the blood parameter. The mathematical model of the multilayer perceptron network is therefore implemented in code C in the microprocessor MP of the probe 2.

Briefly, it is as follows. A neural network model is selected, in other words number of layers, number of neurons for each layer, function of activation of neurons are defined.

Then, it is performed the learning process, using exemplary measures and optimizing the value of the matrixes of the weights and the biases $w_i$ and $b_i$. There is a matrix of weights and biases $w_i$ and $b_i$ for each layer, therefore w1 and b1 are the matrixes of weights and biases of the first layer, w2 and b2 are the matrixes of weights and biases of the second layer, and w3 and b3 are the matrixes of weights and biases of the third layer (and so on if further layers are provided). The terms "optimize", or "optimal values" means finding those values of weights and biases minimizing a cost function which represents the error between the real measure and the predictive measure performed by the network. After defining x_input, in other words the vector containing the values/parameters of the luminescence decay curve (five for the neural network illustrated in Figure and the blood temperature, the algorithm implemented in the probe performs the operations illustrated in FIG. 10B and hereinbefore described.

The developed computing method, which is the result of the machine learning, is substantially an algorithm which is coded and implemented in the microprocessor MP of the probe 2 for performing the measure of the blood parameter. The computing method and also the algorithm are preferably coded in a program code, particularly in code C, and are executed by the microprocessor during the clinical use of the probe 2. Implementing the computing method and the algorithm of the microprocessor MP of the probe 2 makes the probe 2 and consequently the device 1 according to the invention independent in the clinical use; all the computations necessary to measure the blood parameter are performed by the control unit 5 contained in the probe and can be transmitted by a serial cable to the medical machine which it interfaces with, which takes only the "finite datum" of the measure (in other words the datum ready to be used by a medical staff) without performing computations.

It has been verified that probes and therefore devices trained that way have measurement/estimation capability with an accuracy of +/−10% over the entire measurement range, without the need for the end user to perform any calibration point. This means that, when the probe 2 is switched on, it is immediately able to carry out a measurement of the blood parameter with the defined accuracy.

With reference to the training of the neural network for measuring another parameter different from $pO_2$, besides using a specific fluorophore 18' also the neural network to be used for the measure must be specifically defined, once the necessary changes have been made, based on a new complete training by a scheme and mode of collecting data analogous to the ones herein described with reference to the measure of $pO_2$.

Learning Based on the Method of the Fast Determination of the Luminescence Decay Time The learning based on the method of the fast determination of the luminescence decay time comprises the steps of acquiring data, generating data set and subdividing the data set analogous to the beforehand ones described with reference to the machine learning. In addition, it is noted that the laboratory set-up 50 used for performing the herein described learning can be analogous to the beforehand described one or, preferably, can be substantially the same. The difference between the two learning types is the learning itself, because the learning tested and described in this section is not a machine learning. It is understood that in possible embodiments, the method of the fast determination of the luminescence decay time could be used for realizing the machine learning. It is noted that the fast determination of the luminescence decay time is a per se known technique.

Figure 11:
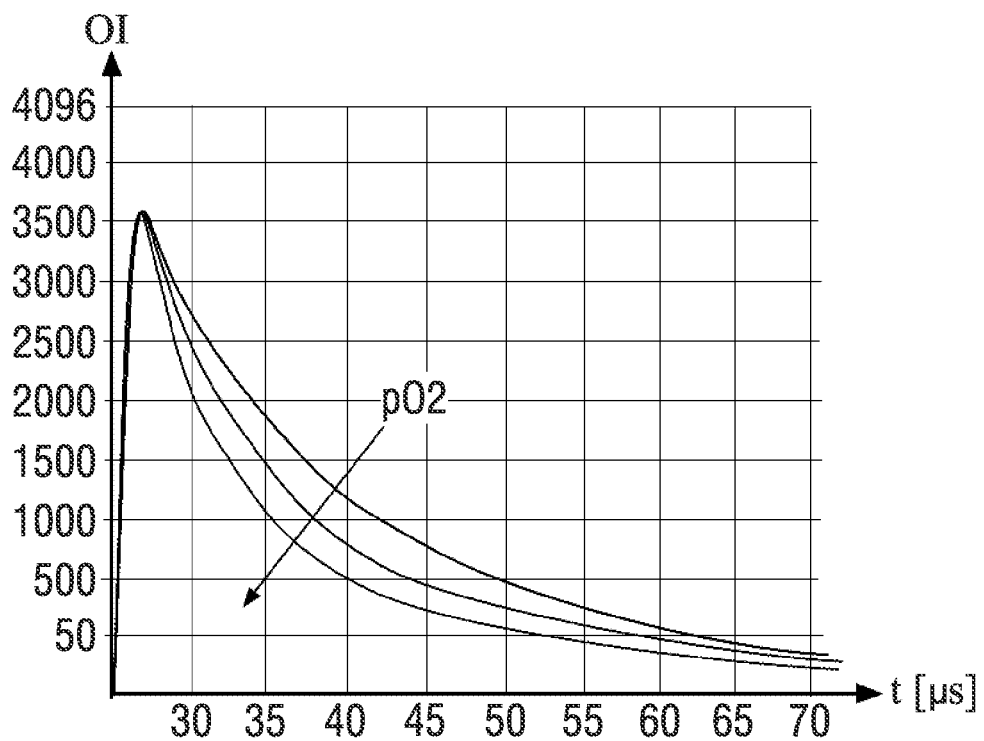
FIG. 11 illustrates a diagram regarding a plurality of luminescence curves, each of them is associated to a different value of partial pressure of oxygen in blood; the arrow with reference $pO_2$ indicates the direction along which the partial pressure of oxygen in blood decreases.
Figure 12:
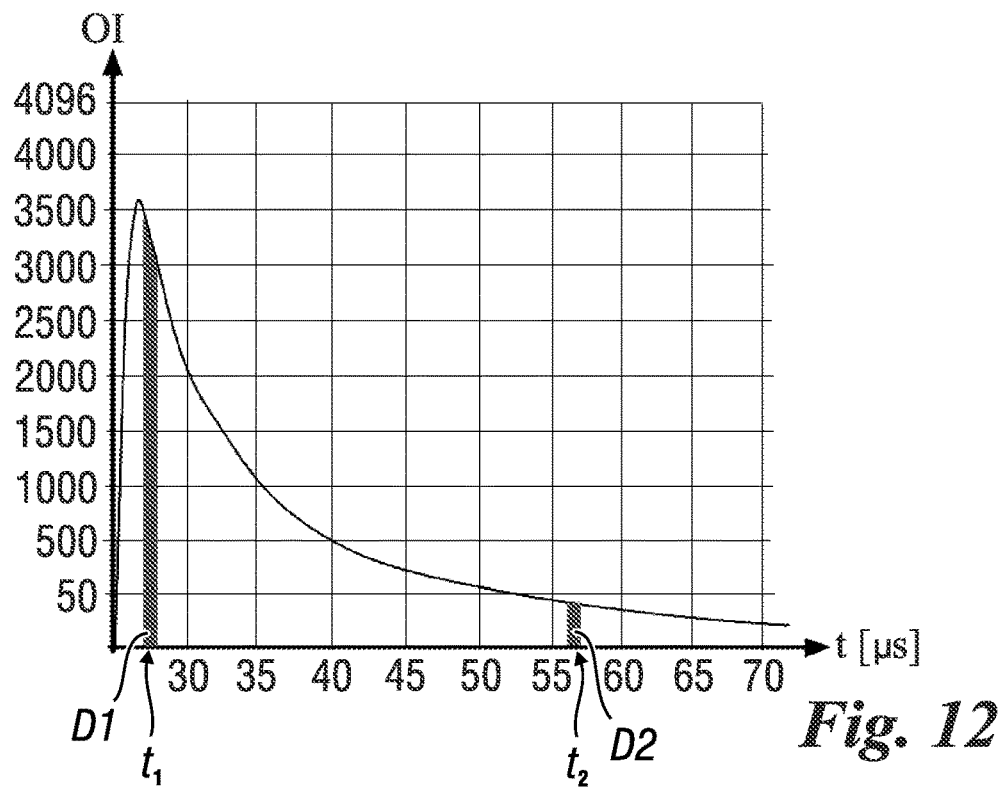
FIG. 12 illustrates a diagram regarding a single luminescence curve, wherein two values of light intensity are outlined; a value (D1) is considered at the start of the decay portion of the curve and the other value (D2) is considered towards a terminal portion of the decay of the curve.

The herein described learning provides to fit the light response digital data and the actual temperature value of blood, preferably by a best-fitting technique, to the plurality of data of previous measures performed in the data acquisition step. The performed tests refer to the training and consequently learning for measuring the parameter $pO_2$; it is noted that the herein described techniques can be applied, once the necessary changes have been made to the measure of another blood parameter. According to such training, the luminescence curves such as those in FIG. 11 are analyzed by converting the luminescence decay curve in a log scale and analyzing the angular coefficient SL of the line obtained by such log conversion; in order to do it, as illustrated in FIG. 12, it is sufficient the analysis of the luminescence decay curve at two time windows t1, t2. Substantially, as illustrated in FIG. 12, for each luminescence decay curve two values D1, D1 of light intensity OI are processed; the first value D1 of the light intensity OI is detected at the beginning of the decay portion of the luminescence curve, while the second value D2 is obtained at the end of the decay portion of the luminescence curve. The angular coefficient SL of the line is function of $pO_2$ and is calculated, for a determined luminescence decay curve as that shown in FIG. 12, as the natural logarithm of the ratio of D1 to D2:

$$SL=\ln(D1/D2)$$

It is performed this computing for a plurality of luminescence curves at different values of the blood actual temperature.

In the scope of the learning method, it is provided a learning step and a step of validating the models. In the learning step, it is used a technique of best-fitting the values of the angular coefficient SL calculated on the average digitized curve expressed by a log scale in two time windows or instants, corresponding to the values D1 and D2 (see FIG. 12) and temporally distanced by an entity varying between 5 and 75 µs; the best-fitting technique is performed by taking into account the actual temperature of blood and the $pO_2$ (measured by the reference blood analyzer 69) based on the group of training data. The step of evaluating the models provides to evaluate the performance of the best-fitting models among the used ones, which distinguish for example in the optimizations of the width and position of the time windows or instants for calculating the angular coefficient. The evaluation is performed on groups of data of tests, in order to select the best model, in other words the model which provides the best results on the group of learning data.

Figure 13:
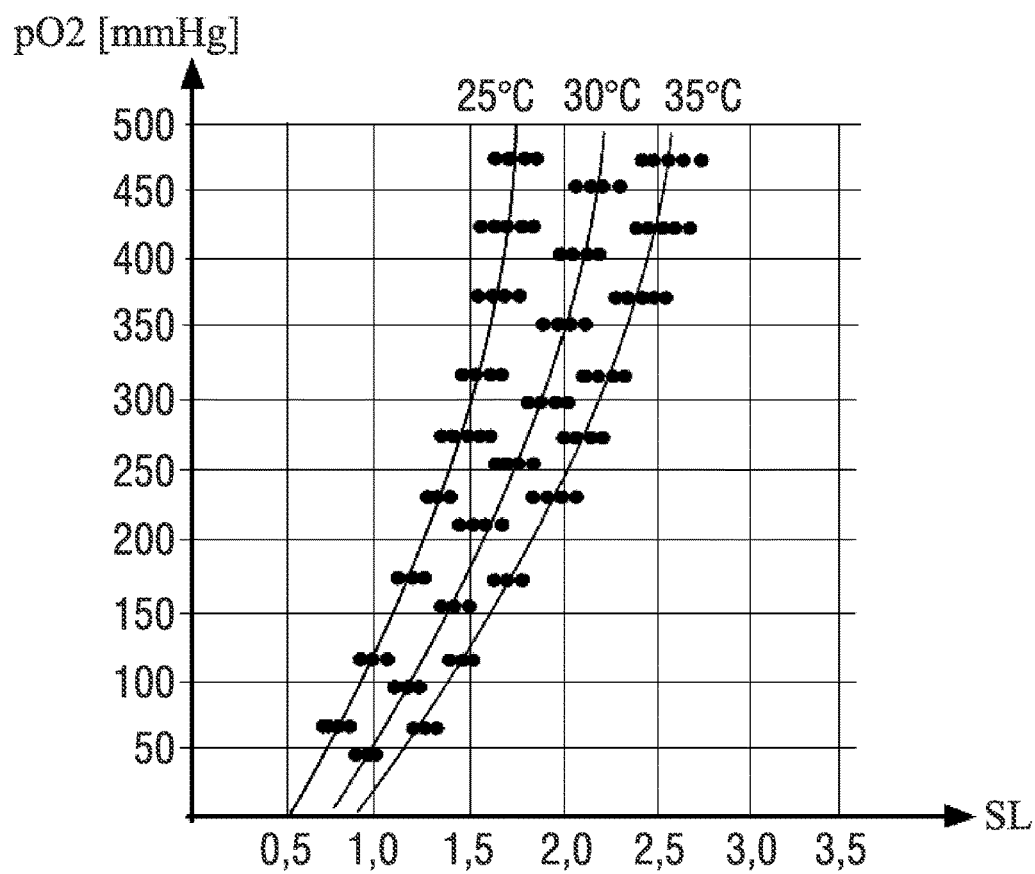
FIG. 13 illustrates a diagram with best-fitting curves, each of them is associated to a different temperature of blood; the curves show the relationship between the partial pressure of oxygen in blood and the angular coefficient of the straight line when the luminescence decay curve is represented in a logarithmic scale.

FIG. 13 shows the graphic correlation between the trend of the $pO_2$ and the value of the angular coefficient SL for three curves at a different value of the actual temperature of blood (25° C., 30°, 35° C.). The points illustrated in the diagram of FIG. 13 represent points of acquisition of luminescence information regarding each curve. The curves illustrated in FIG. 13 are best-fitting curves of the fourth order based on data of the angular coefficient SL calculated for a statistical purpose by many experiments.

Figure 14:
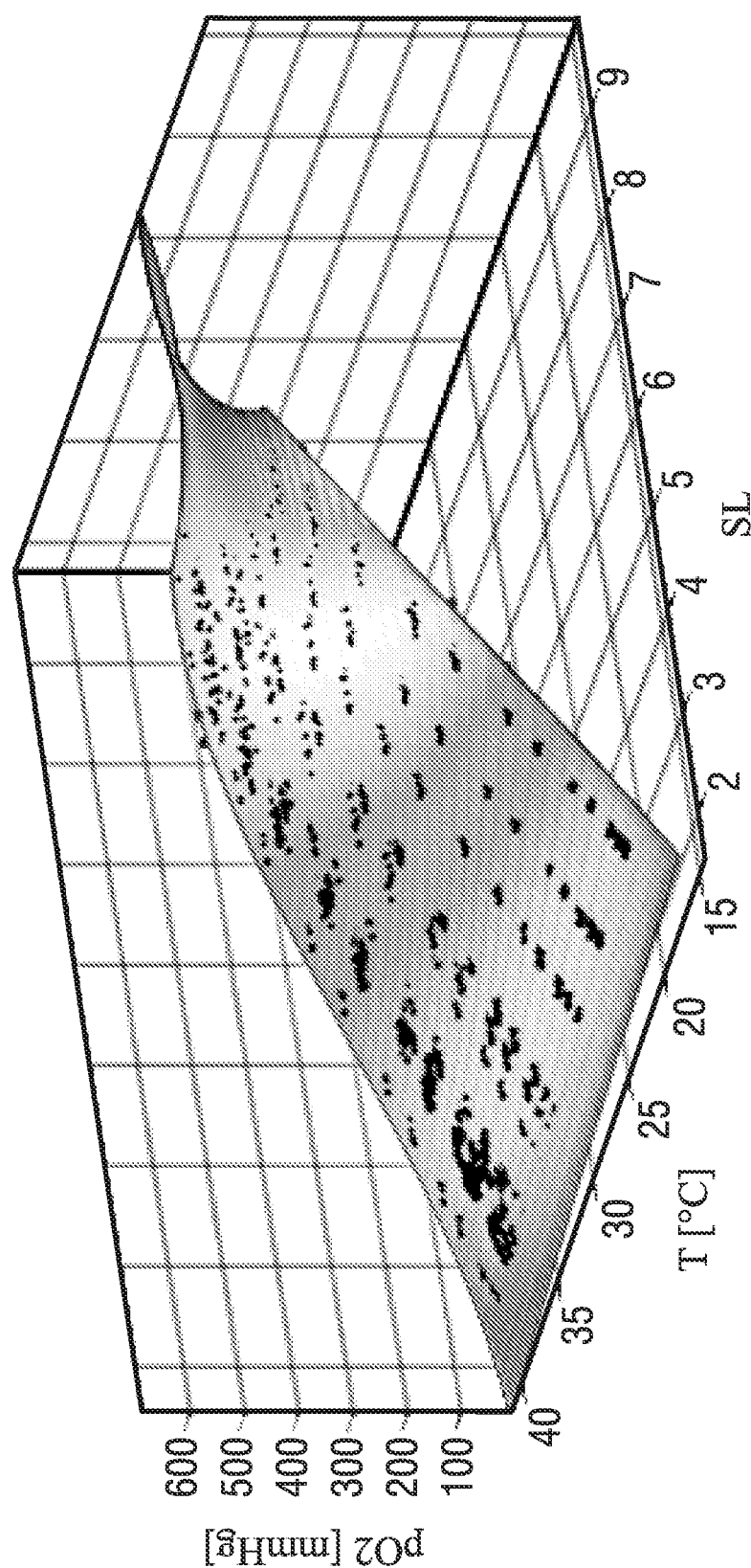
FIG. 14 illustrates a 3D diagram of the best-fitting surface which shows the relationship between the partial pressure of oxygen in blood, temperature and the angular coefficient of the straight line when the luminescence decay curve is represented in a logarithmic scale.

FIG. 14 shows a 3D mathematical representation alternative to the 2D one of FIG. 13. Besides the correlation between $pO_2$ and the value of the angular coefficient SL, FIG. 14 illustrates also the correlation of these two magnitudes with the actual temperature of blood. The 3D diagram of FIG. 14 shows the best-fitting surface; the points illustrated in the diagram are the acquisition points.

Lastly, the learning method provides to verify the selected model on new experimental data in the whole measure range or field, by varying the temperature of blood and a parameter to be measured ($pO_2$, for example). Expect for the type of the selected model, such verifying step is identical to the final step of verifying the model selected in the machine learning method. Substantially, the best-fitting technique provides that the diagram of FIG. 14 "starts" with two values, in other words the value of temperature of blood and the angular coefficient detected for a given luminescence decay curve, and "ends" with the value of the $pO_2$; this last value of $pO_2$ is the value measured by the probe. Therefore, such algorithm is coded in code C in the microprocessor MP of the control unit 5 so that the probe 2 and consequently the device 1 according to the invention, in the clinical use, provides at the output, based on input data regarding the temperature value measured by the temperature sensor of the probe and the angular coefficient calculated by the control unit 5, the value of $pO_2$ of blood at the actual temperature of blood and the value of $pO_2$ at the reference temperature.

Use of the Device

Moreover, the invention refers to a use of the beforehand described device 1. The use of the device 1 is done upon measuring a parameter of blood; the parameter is of a beforehand described type. The use does not require, and therefore does not provide, an initial calibration of the device. Preferably, the use is a clinical use, wherein the device 1 can be used cooperatively with a medical machine 90', 90" such as a heart-lung machine 90' or the extracorporeal membrane oxygenation machine (ECMO) 90", or similar. Due to the training, the device does not require any initial calibration and is therefore of the ready-to-use type.

Figure 7B:
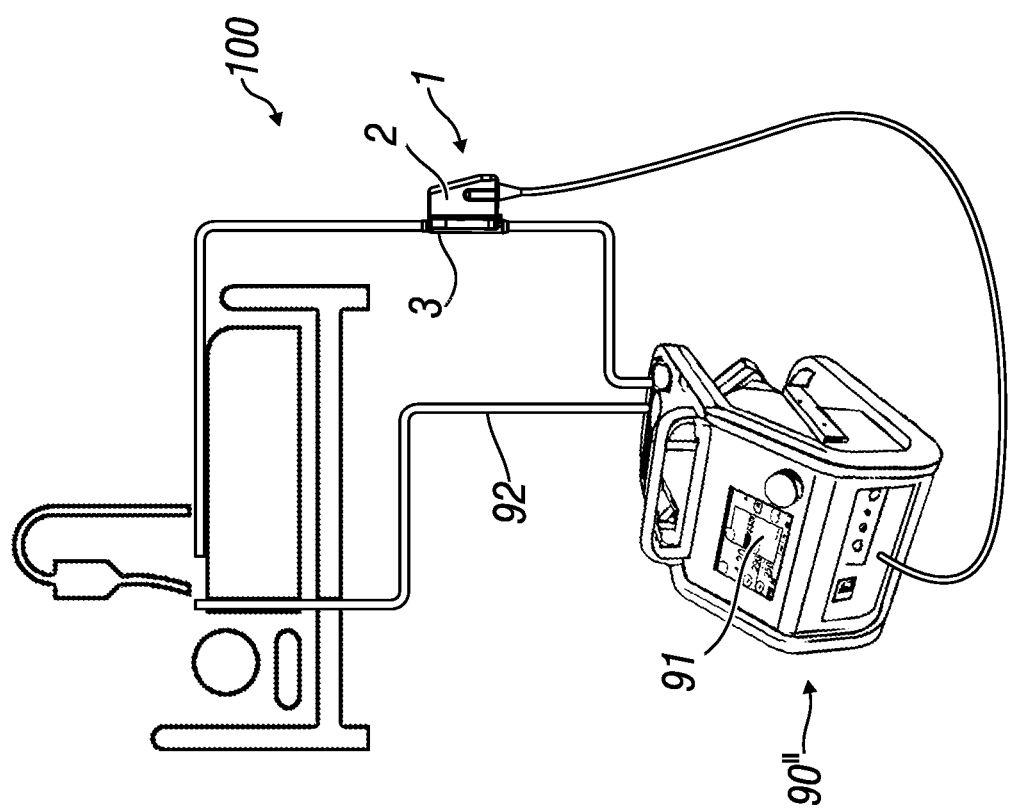
FIG. 7B illustrates another possible clinical use of the device of FIG. 1 in an intensive care unit, wherein the device is used in cooperation with an extracorporeal membrane oxygenation machine (ECMO)
Figure 7A:
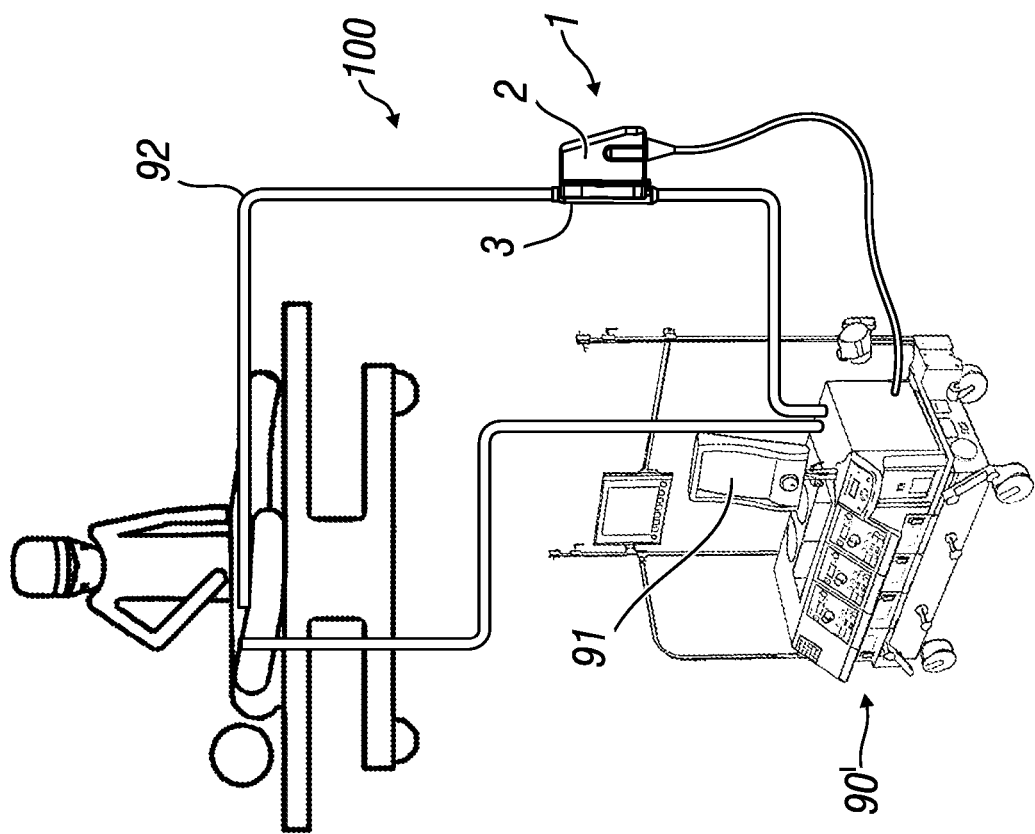
FIG. 7A illustrates a possible clinical use of the device of FIG. 1 in an operating room, where the device is used in cooperation with a heart-lung machine.

FIGS. 7A and 7B illustrate respective apparatuses 100 and possible clinical uses of the device 1 according to the invention. More particularly, FIG. 7A illustrates the clinical use of the device 1 in an operating room, wherein the device 1 is used cooperatively with a heart-lung machine 90', which is connected to. With reference to FIG. 7B, it illustrates the clinical use of the device in an intensive care unit, wherein the device 1 is used cooperatively with an extracorporeal membrane oxygenation machine 90", which is connected to. An example of an intensive care unit in which the device 1 according to the invention can be suitably used is the intensive care for Covid, wherein monitoring one or more parameters correlated to the presence or concentration of oxygen in blood can be crucial.

The value/s of the measured parameter/s is/are made available to the medical staff, for example by a user interface of the medical machine 90', 90". The values of the parameters, both at the actual temperature of blood and at the reference temperature of blood, can be provided to the medical machine 90', 90" on demand by this latter.

Clearly, the device 1 is apt to further clinical uses with respect to the herein described ones, particularly in combination with a further medical machine.

The use of the device can provide, after measuring the parameter of blood by the device 1, to perform an operation of aligning the measured value of the parameter which provides to use an alignment algorithm, as in the following description.

Algorithm for Aligning the Measured Values of the Blood Parameter

Moreover, a correction of the value of the parameter measured by the device 1 (therefore by the probe 2) can be carried out, as follows. Such correction can be performed by an alignment algorithm which can be applied independently from the learning mode of the probe 2. Therefore, the alignment algorithm can be applied both to a probe which was subjected to a machine learning and to a probe which was subjected to a learning based on the method of the fast determination of the luminescence decay time, according to the beforehand described learning modes. The alignment algorithm, which will be described in the following, is an option available to the end user (i.e. available to the customer of the supplier responsible for the calibration of the probe) for aligning the measured value of the probe 2 with the ones obtained by a reference instrument available to the end user, as described in the following. Such possibility provided by the probe is useful for some types of users (such as the ones desiring to perform a calibration of the probe 2 by using a reference instrument which they consider particularly reliable) because it enables the end user, during the use of the device 1 and after performing the measure of the parameter, to align the value of the measured parameter. It is noted that the possibility of the alignment is quite optional and that the device 1 according to the invention already provides a high accuracy and reliability of the measure. Further, it is noted that the alignment is subjected to the percentage correction limits which will be described in the following.

Substantially, it is possible to provide an algorithm for aligning the value of the parameter (such as the partial pressure of oxygen in blood) measured by the probe 2 with the value recorded by a parameter reference instrument employed by the end user of the probe 2. Such reference instrument, available to the end user, can be of a type analogous to the one used by the supplier of the probe 2 for the learning step; this latter instrument was previously exemplified by a reference blood analyzer 69. An example of a reference instrument for aligning the value of the parameter is a reference blood analyzer used by the end user of the probe 2; when the present section regarding the alignment algorithm mentions the reference instrument it means the one in use by the end user of the probe 2. The parameter which is considered in the following is the partial pressure of oxygen in blood; however, this does not exclude the possibility of applicating the algorithm to other parameters.

The algorithm for aligning the value of $pO_2$ measured by the probe 2, with the one of the reference instrument used by the user of the probe 2 is performed by executing two commands, in other words the command "Store", which is supplied to the probe 2 from the control unit of the medical machine 90', 90" which it is connected to in conditions of use when it is performed a draw of blood to be analyzed by said reference instrument, and the command "Recall" which is lastly supplied to the probe 2 as soon as the results of the blood sample measured by the reference instrument are available. It is not excluded to use analogous and/or different commands, or a number of commands greater than two.

When the command "Store" is sent, the probe 2 performs the acceptance tests by verifying the measured parameters fall into the measure ranges given both for $pO_2$ and for the blood temperature ($T_{blood}$). The object of these tests is to verify that the probe 2 is measuring $pO_2$ in the range mmHg and 0.400 mmHg and the blood temperature in the range 15° C. and 0.40° C.

If these tests are passed, the parameters of the present measure of $pO_2$ (both at the actual temperature and at 37° C.) and of the blood temperature, measured by the probe 2, are stored in an allocated space of a random access memory (RAM) of the probe 2. This memory space is created during the start-up routine for the probe 2 and will contain the $pO_2$ and blood temperature ($T_{blood}$) parameters relative to the command "Store" and the reference $pO_2$, regarding the command "Recall"; such values are then transferred from the control unit which the probe 2 is connected to.

After executing the command "Store", the probe 2 continues to normally operate according to its calibration parameters until the command "Recall". By the command "Recall", the data of $pO_2$ measured by the reference instrument are transferred to the firmware of the probe 2 by the control unit which is connected to.

The parameters to be sent to the probe 2 are the values of $pO_2$ measured at 37° C.

The command "Recall" can be given only after executing a command "Store". When the command "Recall" is sent, the alignment algorithm is executed. The alignment algorithm is applied/executed only if the percentage error of the probe 2 with respect to the reference instrument is 3% (an error less than 3% could be caused by the variability of the reference instruments) and the correction to be performed is limited to a maximum of 6% (the device 1 according to the invention supplies an accurate measure of the parameter and therefore offsets greater than 6% are excluded).

The alignment algorithm provides a percentage (%) correction of the reading of $pO_2$ by the probe 2 from the instant in which the command "recall" is executed to a possible new alignment procedure, which is selected at discretion of the user.

The correction is applied both to the $pO_2$ measured at 37° C. and to the one of the actual temperature of blood.

Two examples are given in the following.

Case 1
the value of $pO_2$ measured by the device at 37° C., when the command "Store" is performed is 83 mmHg
the value measured by the reference instrument is 95 mmHg at 37° C.
the error by percentage is −12.6%
the value measured by the instrument when the command "Recall" is performed is 150 mmHg at 37° C.

the algorithm introduces a correction limited to 6%, in other words the value of 150 mmHg is corrected to 141 mmHg.

Case 2 the value of $pO_2$ measured by the device at 37° C., when the command "Store" is performed is 195 mmHg the value measured by the reference instrument is 190 mmHg at 37° C.

the error by percentage is +2.6% the correction is not applied since the error by percentage is less than 3%.

Performing the commands "Store" and "Recall" is part of an alignment cycle which enables to perform the correction of the measured value as herein before described.

The alignment, if it is performed, occurs necessarily after taking a measure of the parameter and, when required and at discretion of the end user, can be also performed many times after a single measure. Each possible repetition of the alignment cycle which occurs by said commands can happen only after the end of the previous alignment cycle (and therefore only after correcting the value of the parameter performed by the previous alignment cycle).

It is noted that the beforehand described alignment is not a calibration of the device 1; indeed, it comprises, to some extent, the correction of the measured value, while it does not comprise any change to the method by which the device 1 measures the value of the parameter (the measuring method being obtained by the previous training performed in laboratory and the user being not capable of modifying it). Consequently, the device 1 provided to the user is immediately ready to be used for performing one or more measures of the parameter; the end user evaluates then, in a completely arbitrary way, whether perform the alignment and therefore the correction of the measured parameter.

Apparatus

Moreover, the invention refers to an apparatus 100 comprising a device 1 of the beforehand described type and to a medical machine 90', 90". The device 1 is configured to cooperate and communicate with the medical machine 90', 90".

The medical machine 90', 90" can be a heart-lung machine 90' or an extracorporeal membrane oxygenation machine 90" or another type of medical machine. The medical machine 90', 90" can comprise a user interface configured to provide the values of the parameters measured by the probe 2. The user interface can include a display means 91, such as a screen apt to show such values. The display means 91 is operatively connected or connectable to the device 1. The display means 91 can be part of, or be associated or associable to, the medical machine. FIGS. 7A and 7B show medical machines 90', 90" in which the display means 91 is embodied by a screen integrated in the medical machine 90', 90". Alternatively, the user interface can make available or communicate the values of the parameters to the medical staff in another way.

The apparatus 100 comprises a blood extracorporeal circuit 92 configured to circulate blood. The blood extracorporeal circuit 92 connects the medical machine 90', 90" to the patient and the tubular element 3 of the device 1 is placed along the blood extracorporeal circuit 92 (see FIGS. 7A and 7B). In operative conditions (clinical use) of the apparatus, the photosensitive element 18' is in contact with blood in order to enable the device 1 to measure one or more parameters of blood. Substantially, the device 1 can be an appendage of the medical machine 90', 90" which operatively acts as a sensor destined to measure one or more parameters of blood circulating in the blood extracorporeal circuit 92.

Method of Measuring a Parameter of Blood

Moreover, the present invention refers to a method of measuring a parameter of blood. The parameter is of the beforehand described type. Preferably, the method provides to use a device 1 of the beforehand described type: the steps described in the following can be performed by corresponding components of the device 1 apt to accomplish the corresponding function. Preferably, the implementation of the steps is determined and/or supervised by the control unit 5 of the probe 2.

The method provides to excite a photosensitive element 18' in contact with blood circulating in a blood extracorporeal circuit 92 by a series of excitation pulses. Preferably, such step is performed by the excitation member 10 and the photosensitive element 18' is preferably associated to a container 3, particularly a tubular element such as a cuvette. As previously said, the photosensitive element is preferably a photosensitive substance.

Therefore, the method provides to terminate the excitation step between consecutive pulses of the series of excitation pulses; substantially, it is emitted a pulse, then there is a brief interruption, it is emitted another pulse, and so on to the end of the series of pulses.

A plurality of light responses of the photosensitive element 18' corresponding to the series of excitation pulses are detected; each light response provides a respective luminescence decay curve. Particularly, at the end of each pulse, it is detected the light response of the photosensitive element 18'. So, the detection step is implemented when the excitation by the excitation member 10 is not in progress.

The method provides to analyze the plurality of luminescence decay curves. Such step provides to analyze each luminescence decay curve at at least two time windows t1, t2; the number N, the duration, the distance, and variation of the time windows t1-tN can be according to what was beforehand described.

Therefore, one or more light response analog information regarding the luminescence decay curve are detected at each time window. The light response analog information, detected at at least two time windows t1, t2 for each light response, are consequently converted into light response digital data. Preferably the conversion is performed by the analog-digital converter.

Further, the method provides to detect the actual temperature value of blood. Preferably, such step is implemented by the temperature sensor 15 contained in the probe.

Consequently, the method provides to process the light response digital data and the actual temperature value of blood by taking into account a plurality of data of previous measures of the blood parameter performed during a previous training. The method takes into account the previous measures preferably by an algorithm, of the beforehand described type or of another type. The previous training can be according to one of the beforehand described modes, or to further modes. Preferably, the processing step is performed by executing a program code, based on machine learning or similar, and obtained by previous training. The execution of the program code is performed by a microprocessor MP of the probe 2 according to what was beforehand described. Processing the light response digital data and the actual temperature value of blood can be performed by analyzing the light response digital data and the actual temperature value of blood by a matrix mathematical model or fitting the light response digital data and the actual temperature value of blood to the plurality of data of previous measures made during a previous training.

As a result of the processing step, it is determined, in other words measured, at least one value of the blood parameter. Specifically, such step provides to determine both the value of the parameter at the actual temperature of blood and the value of the parameter at a reference temperature of blood, for example at 37° C.

As beforehand described with reference to the device, processing light response digital data and the value of actual temperature of blood provides to take into account a plurality of data of previous measures of the blood parameter performed during a previous training done by using a plurality of photosensitive elements 18' provided with the same chemical composition.

Since the probe 2 is ready to be used, the method does not provide a step of calibrating the device 1.

Moreover, it is noted that, before the excitation step, the method can provide the step of coupling the container 3 to the coupling portion 7 of the probe 2. The modes of specifically coupling the probe 2 to the tubular element 3 of the device 1 illustrated in Figures from 1 to 6 are described in the following; it is understood that other coupling possibilities can be provided. The coupling step provides to couple the tubular element 3 to the probe 2 by first coupling elements 8, 21 and by second coupling elements 9, 22. The single coupling steps by first coupling elements 8, 21 and second coupling elements 9, 22 are preferably performed at respective opposite ends of the coupling portion 7 and of the tubular element 3. The coupling step by the first coupling elements 8, 21 is preferably performed before the step of coupling by second coupling elements 9, 22. The coupling step by first coupling elements 8, 21 can provide to insert a tab or hook 8 of the coupling portion 7 into a corresponding slit 21 of the tubular element 3. The coupling step by the second coupling elements 9, 22 can provide to magnetically couple the coupling portion 7 to the tubular element 3 by respective magnets 9, 22. Substantially, for coupling the tubular element 3 to the probe 2, first of all the hook 8 is inserted into the slit 21 (mechanical coupling) and then the respective magnets 9, 22 of the probe 2 and tubular element 3 are coupled (magnetic coupling). The magnetic coupling, subsequent to the mechanical coupling, determines a rotation of the tubular element 3 towards the magnet 9 of the coupling portion 7; the rotation of the tubular element 3 is performed about a rotation center implemented by the end of the tubular element 3 beforehand mechanically engaged with the coupling portion 7 by the first coupling elements 8, 21. The magnetic attraction force between the magnets 9, 22 determines a substantially snap-fit between the probe 2 and the tubular element 3.

The technical characteristics herein disclosed with reference to steps of the method can be applied to the scope of corresponding functions or uses of the device 1 beforehand described and therefore can be employed for specifying such functions or uses in the attached claims.

Briefly stated, the main advantages of the invention are the following:
the measurement of the parameter is performed without requiring the end user to calibrate the probe 2,
the device 1 is autonomous from the point of view of the measurement, i.e. it does not depend on other instrumentation external with respect to the device 1 itself for carrying out the measurement of the parameter,
the measurement is reliable in the whole field of measure of the parameter and has an accuracy of +/−10% in the entire field of measure,
the measure is performed by a compact, small-sized light device 1, the components thereof being suitably miniaturized.

The invention claimed is:

1. A device for measuring a blood parameter, preferably related to the presence or concentration of oxygen in blood, comprising:
a box body,
a coupling portion associated to the box body and comprising at least one coupling element, the coupling portion being configured to feature:
a coupled configuration wherein it is coupled to a container by said at least one coupling element,
a decoupled configuration wherein it is not coupled to a container,
a container, for example a tubular element, apt to contain blood and/or in which blood can flow, the container being configured to be coupled to said coupling portion,
a photosensitive element associated to the container and apt to respond, at the end of an excitation to which it is subjected when it is in contact with blood, with a light response, the light response providing a luminescence decay curve, in operative conditions the photosensitive element being in contact with blood,
an excitation member housed inside the box body and configured to excite said photosensitive element by a series of excitation pulses,
a photodetector housed inside the box body and configured to detect, in operative conditions of the device, a plurality of light responses of the photosensitive element corresponding to the series of excitation pulses, the light responses providing luminescence decay curves, and
a control unit housed inside the box body and configured to perform the following operations:
receiving, for each of at least two time windows in which each luminescence curve is analyzed, one or more light response analog information regarding the luminescence decay curve,
converting the light response analog information, detected at least two time windows for each light response, into light response digital data,
processing said light response digital data and the actual temperature value of blood by considering a plurality of data of previous measures of said blood parameter performed during previous training,
determining, as a result of the processing operation, at least one value of said blood parameter.

2. The device according to claim 1, wherein the photosensitive element is provided with a determined chemical composition, the control unit being configured to consider a plurality of data of previous measures of said blood parameter performed during previous training carried out by using a plurality of photosensitive elements having the same chemical composition.

3. The device according to claim 1, wherein the control unit is configured to:
determine, as a result of the processing operation, a value of said parameter at the blood actual temperature, and
determine, as a result of the processing operation, a value of said parameter at a blood reference temperature, for example 37° C.

4. The device according to claim 1, the device being of a ready to use and/or plug-and-play type, said device being useable without requiring an initial calibration, and/or said device being calibrated during previous laboratory training.

5. The device according to claim 1, wherein the control unit is configured to consider a plurality of data of previous measures of said blood parameter, performed during previous training, by a program code based on machine learning and obtained by previous training.

6. The device according to claim 5, wherein the machine learning, thus the program code, is calibrated on the chemical composition of the photosensitive element.

7. The device according to claim 1, wherein the control unit is configured to process said light response digital data and said actual temperature value of blood by considering a plurality of data of previous measures of said blood parameter by means of an algorithm, preferably the algorithm deriving from previous training, the algorithm having at least two suitable output data, said two suitable output data providing:
the value of said parameter at the actual temperature value of blood,
the value of said parameter at a blood reference temperature, for example 37° C.

8. The device according to claim 1, wherein the control unit is configured to perform one or more of the following operations:
analyzing said light response digital data and said blood actual temperature value by a matrix mathematical model, and/or
fitting said light response digital data and said blood actual temperature value to the plurality of data of previous measures.

9. The device according to claim 1, wherein the coupling portion and the container comprise a respective coupling element of a first type and a respective coupling element of a second type, in the coupled configuration the first type coupling elements being coupled to each other and the second type coupling elements being coupled to each other,
optionally the coupling portion and the container providing that the respective first type coupling element and respective second type coupling element are defined at or in proximity of their opposite ends.

10. The device according to claim 9, the coupling elements of the first type being configured for allowing mechanical engagement of the container to the coupling portion of the device, and the coupling elements of the second type being configured for allowing magnetic engagement of the container to the coupling portion of the device.

11. The device according to claim 1, wherein the photosensitive element is of disposable type.

12. An apparatus comprising:
a device comprising:
a box body,
a coupling portion associated to the box body and comprising at least one coupling element, the coupling portion being configured to feature:
a coupled configuration wherein it is coupled to a container by said at least one coupling element,
a decoupled configuration wherein it is not coupled to a container,
a container, for example a tubular element, apt to contain blood and/or in which blood can flow, the container being configured to be coupled to said coupling portion,
a photosensitive element associated to the container and apt to respond, at the end of an excitation to which it is subjected when it is in contact with blood, with a light response, the light response providing a luminescence decay curve, in operative conditions the photosensitive element being in contact with blood,
an excitation member housed inside the box body and configured to excite said photosensitive element by a series of excitation pulses,
a photodetector housed inside the box body and configured to detect, in operative conditions of the device, a plurality of light responses of the photosensitive element corresponding to the series of excitation pulses, the light responses providing luminescence decay curves, and
a control unit housed inside the box body and configured to perform the following operations:
receiving, for each of at least two time windows in which each luminescence curve is analyzed, one or more light response analog information regarding the luminescence decay curve,
converting the light response analog information, detected at least two time windows for each light response, into light response digital data,
processing said light response digital data and the actual temperature value of blood by considering a plurality of data of previous measures of said blood parameter performed during previous training,
determining, as a result of the processing operation, at least one value of said blood parameter,
a medical machine, for example a heart-lung machine or an extracorporeal membrane oxygenation machine, and
a user interface such as a display means, operatively connected or connectable to the device and configured to provide said at least one value of said blood parameter.

13. A method of measuring a blood parameter, preferably related to the presence or concentration of oxygen in blood, comprising the steps of:
exciting a photosensitive element in contact with blood by a series of excitation pulses, blood circulating in an extracorporeal blood circuit,
dimming or terminating the excitation step between consecutive pulses of the series of excitation pulses,
detecting a plurality of light responses of the photosensitive element corresponding to the series of excitation pulses, the light responses providing respective luminescence decay curves,
analyzing the plurality of luminescence decay curves, said step providing to analyze each luminescence decay curve at a least two time windows,
detecting one or more light response analog information regarding the decay of the luminescence curve at each time window,
converting the light response analog information, detected during at least two time windows for each light response, into light response digital data,
processing said light response digital data and the actual temperature value of blood considering a plurality of data of previous measures of said blood parameter performed during previous training, and
determining, as a result of the processing step, at least one value of said blood parameter.

14. The method according to claim 13, wherein:
the photosensitive element is provided with a determined chemical composition,
the step of processing said light response digital data and the actual temperature value of blood considering a plurality of data of previous measures of said blood parameter performed during previous training providing to consider a plurality of data of previous measures of said blood parameter performed during previous training carried out by using a plurality of photosensitive elements having the same chemical composition.

15. The method according to claim 13, wherein the step of determining, as a result of the processing step, at least one value of said blood parameter comprises:
determining, based on said light response digital data, a value of said parameter at the blood actual temperature,
determining, based on said light response digital data, a value of said parameter at a blood reference temperature, for example, 37° C.

16. The method according to claim 13, wherein the step of processing said light response digital data and the blood actual temperature value by considering a plurality of data of previous measures of said blood parameter is performed by a program code based on machine learning and obtained by previous training.

17. The method according to claim 13, wherein the step of processing said light response digital data and the blood actual temperature value by considering a plurality of data of previous measures of said blood parameter is carried out by means of an algorithm, preferably the algorithm deriving from previous training and being based on learning, preferably machine learning, the training and thus the learning being carried out before the use of the device, preferably during a plurality of training periods.

18. The method according to claim 13, wherein the step of processing said light response digital data and the blood actual temperature value by considering a plurality of data of previous measures of said blood parameter comprises one or more of the following steps:
analyzing said light response digital data and said blood actual temperature value by a matrix mathematical model, and/or
fitting said light response digital data and said blood actual temperature value to the plurality of data of previous measures.

19. The method according to claim 13, comprising, before the excitation step, the following steps:
predisposing a device according to claim 1,
coupling a container to a coupling portion of the device, said coupling step comprising the steps of:
coupling the container to the device by first coupling elements, and
coupling the container to the device by second coupling elements,
the coupling steps by the first coupling elements and by second coupling elements being performed at respective opposite ends of the coupling portion and of the container.

20. The method according to claim 13, wherein the analysis of each luminescence decay curve is an analysis in the time domain.

* * * * *